(12) United States Patent
Lanphere et al.

(10) Patent No.: US 9,283,035 B2
(45) Date of Patent: *Mar. 15, 2016

(54) TISSUE-TREATMENT METHODS

(71) Applicant: Boston Scientific Scimed, Inc., Maple Grove, MN (US)

(72) Inventors: Janel L. Lanphere, Flagstaff, AZ (US); Paul DiCarlo, Middleboro, MA (US); Steven M. Anderson, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 13 days.

This patent is subject to a terminal disclaimer.

(21) Appl. No.: 13/872,521

(22) Filed: Apr. 29, 2013

(65) Prior Publication Data

US 2013/0237981 A1    Sep. 12, 2013

Related U.S. Application Data

(63) Continuation of application No. 13/106,563, filed on May 12, 2011, now Pat. No. 8,430,105, which is a continuation of application No. 11/117,156, filed on Apr. 28, 2005, now Pat. No. 7,963,287.

(51) Int. Cl.
*A61B 19/00* (2006.01)
*A61B 18/18* (2006.01)
(Continued)

(52) U.S. Cl.
CPC ............... *A61B 18/18* (2013.01); *A61B 19/40* (2013.01); *A61L 27/3683* (2013.01); *A61B 18/14* (2013.01);
(Continued)

(58) Field of Classification Search
CPC ........ A61B 18/00; A61B 18/04; A61B 18/12; A61B 18/14; A61B 2018/00005; A61N 1/00; A61N 1/0404; A61N 1/06; A61N 1/40; A61N 5/00; A61N 5/06; A61N 7/00; A61N 2007/0004; A61L 27/36; A61L 27/3683; A61L 27/3687
USPC .............. 607/88–93, 96–107; 606/13–16, 27; 128/898
See application file for complete search history.

(56) References Cited

U.S. PATENT DOCUMENTS

| 2,275,154 A | 3/1942 | Merrill |
| 2,609,347 A | 9/1952 | Wilson |

(Continued)

FOREIGN PATENT DOCUMENTS

| AU | A7618698 | 10/1998 |
| DE | 3834705 | 4/1990 |

(Continued)

OTHER PUBLICATIONS

"Fibroid Treatment Collective Fibroid Embolization," 2 pages, http://www.fibroids.org.

(Continued)

*Primary Examiner* — Ahmed Farah
(74) *Attorney, Agent, or Firm* — Kacvinsky Daisak Bluni PLLC

(57) ABSTRACT

Polymer insulators and methods of using polymer insulators are disclosed. In some embodiments, a method includes separating a first portion of a subject's tissue from a second portion of the subject's tissue so that there is a space between the first and second portions of tissue. Deionized water, a buffered saline solution, liquid polymers, gels, particles, foams, and/or gases are disposed between the first and second portions of tissue, and the first portion of tissue is exposed to energy to treat the first portion of tissue.

20 Claims, 4 Drawing Sheets

(51) Int. Cl.
  *A61L 27/36* (2006.01)
  *A61B 18/14* (2006.01)
  *A61B 17/00* (2006.01)
  *A61N 7/02* (2006.01)
(52) U.S. Cl.
  CPC ..... *A61B 2017/008* (2013.01); *A61B 2019/409* (2013.01); *A61B 2019/4072* (2013.01); *A61B 2019/4081* (2013.01); *A61N 7/02* (2013.01)

(56) References Cited

U.S. PATENT DOCUMENTS

| | | |
|---|---|---|
| 3,663,470 A | 5/1972 | Nishimura |
| 3,737,398 A | 6/1973 | Yamaguchi |
| 3,957,933 A | 5/1976 | Egli |
| 4,025,686 A | 5/1977 | Zion |
| 4,034,759 A | 7/1977 | Haerr |
| 4,055,377 A | 10/1977 | Erickson |
| 4,076,640 A | 2/1978 | Forgensi |
| 4,094,848 A | 6/1978 | Naito |
| 4,096,230 A | 6/1978 | Haerr |
| 4,098,728 A | 7/1978 | Rosenblatt |
| 4,110,529 A | 8/1978 | Stoy |
| 4,159,719 A | 7/1979 | Haerr |
| 4,191,672 A | 3/1980 | Salome |
| 4,198,318 A | 4/1980 | Stowell |
| 4,243,794 A | 1/1981 | White |
| 4,246,208 A | 1/1981 | Dundas |
| 4,266,030 A | 5/1981 | Tschang |
| 4,268,495 A | 5/1981 | Muxfeldt |
| 4,271,281 A | 6/1981 | Kelley |
| 4,402,319 A | 9/1983 | Handa |
| 4,413,070 A | 11/1983 | Rembaum |
| 4,427,794 A | 1/1984 | Lange |
| 4,428,869 A | 1/1984 | Munteanu |
| 4,429,062 A | 1/1984 | Pasztor |
| 4,442,843 A | 4/1984 | Rasor |
| 4,444,961 A | 4/1984 | Timm |
| 4,452,773 A | 6/1984 | Molday |
| 4,456,693 A | 6/1984 | Welsh |
| 4,459,145 A | 7/1984 | Elsholz |
| 4,472,552 A | 9/1984 | Blouin |
| 4,477,255 A | 10/1984 | Pasztor |
| 4,492,720 A | 1/1985 | Mosier |
| 4,515,906 A | 5/1985 | Friesen |
| 4,522,953 A | 6/1985 | Barby |
| 4,542,178 A | 9/1985 | Zimmermann |
| 4,551,132 A | 11/1985 | Pasztor |
| 4,551,436 A | 11/1985 | Johnson |
| 4,573,967 A | 3/1986 | Hargrove |
| 4,622,362 A | 11/1986 | Rembaum |
| 4,623,706 A | 11/1986 | Timm |
| 4,629,464 A | 12/1986 | Takata |
| 4,640,807 A | 2/1987 | Afghan |
| 4,657,756 A | 4/1987 | Rasor |
| 4,661,137 A | 4/1987 | Garnier |
| 4,663,358 A | 5/1987 | Hyon |
| 4,671,954 A | 6/1987 | Goldberg |
| 4,671,994 A | 6/1987 | Cochran |
| 4,674,480 A | 6/1987 | Lemelson |
| 4,675,113 A | 6/1987 | Graves |
| 4,678,710 A | 7/1987 | Sakimoto |
| 4,678,814 A | 7/1987 | Rembaum |
| 4,680,320 A | 7/1987 | Uku |
| 4,681,119 A | 7/1987 | Rasor |
| 4,695,466 A | 9/1987 | Morishita |
| 4,713,076 A | 12/1987 | Draenert |
| 4,742,086 A | 5/1988 | Masamizu |
| 4,743,507 A | 5/1988 | Franses |
| 4,772,635 A | 9/1988 | Mitschker |
| 4,782,097 A | 11/1988 | Jain |
| 4,789,501 A | 12/1988 | Day |
| 4,793,980 A | 12/1988 | Torobin |
| 4,795,741 A | 1/1989 | Leshchiner |
| 4,801,458 A | 1/1989 | Hidaka |
| 4,804,366 A | 2/1989 | Zdeb |
| 4,819,637 A | 4/1989 | Dormandy |
| 4,822,535 A | 4/1989 | Ekman |
| 4,833,237 A | 5/1989 | Kawamura |
| 4,850,978 A | 7/1989 | Dudar |
| 4,859,711 A | 8/1989 | Jain |
| 4,863,972 A | 9/1989 | Itagaki |
| 4,889,129 A | 12/1989 | Dougherty |
| 4,897,255 A | 1/1990 | Fritzberg |
| 4,929,400 A | 5/1990 | Rembaum |
| 4,933,372 A | 6/1990 | Feibush |
| 4,946,899 A | 8/1990 | Kennedy |
| 4,954,399 A | 9/1990 | Tani |
| 4,981,625 A | 1/1991 | Rhim |
| 4,990,340 A | 2/1991 | Hidaka |
| 4,999,188 A | 3/1991 | Solodovnik |
| 5,007,940 A | 4/1991 | Berg |
| 5,011,677 A | 4/1991 | Day |
| 5,015,423 A | 5/1991 | Eguchi |
| 5,032,117 A | 7/1991 | Motta |
| 5,034,324 A | 7/1991 | Shinozaki |
| 5,047,438 A | 9/1991 | Feibush |
| 5,079,274 A | 1/1992 | Schneider |
| 5,091,205 A | 2/1992 | Fan |
| 5,106,903 A | 4/1992 | Vanderhoff |
| 5,114,421 A | 5/1992 | Polak |
| 5,116,387 A | 5/1992 | Berg |
| 5,120,349 A | 6/1992 | Stewart |
| 5,125,892 A | 6/1992 | Drudik |
| 5,147,631 A | 9/1992 | Glajch |
| 5,147,937 A | 9/1992 | Frazza |
| 5,149,543 A | 9/1992 | Cohen |
| 5,151,096 A | 9/1992 | Khoury |
| 5,158,573 A | 10/1992 | Berg |
| 5,171,214 A | 12/1992 | Kolber |
| 5,171,217 A | 12/1992 | March |
| 5,181,921 A | 1/1993 | Makita |
| 5,190,760 A | 3/1993 | Baker |
| 5,190,766 A | 3/1993 | Ishihara |
| 5,192,301 A | 3/1993 | Kamiya |
| 5,202,352 A | 4/1993 | Okada |
| 5,216,096 A | 6/1993 | Hattori |
| 5,236,410 A | 8/1993 | Granov |
| 5,253,991 A | 10/1993 | Yokota |
| 5,260,002 A | 11/1993 | Wang |
| 5,262,176 A | 11/1993 | Palmacci |
| 5,263,992 A | 11/1993 | Guire |
| 5,288,763 A | 2/1994 | Li |
| 5,292,814 A | 3/1994 | Bayer |
| 5,302,369 A | 4/1994 | Day |
| 5,314,974 A | 5/1994 | Ito |
| 5,316,774 A | 5/1994 | Eury |
| RE34,640 E | 6/1994 | Kennedy |
| 5,320,639 A | 6/1994 | Rudnick |
| 5,328,936 A | 7/1994 | Leifholtz |
| 5,336,263 A | 8/1994 | Ersek |
| 5,344,452 A | 9/1994 | Lemperle |
| 5,344,867 A | 9/1994 | Morgan |
| 5,354,290 A | 10/1994 | Gross |
| 5,369,133 A | 11/1994 | Ihm |
| 5,369,163 A | 11/1994 | Chiou |
| 5,382,260 A | 1/1995 | Dormandy |
| 5,384,124 A | 1/1995 | Courteille |
| 5,397,303 A | 3/1995 | Sancoff |
| 5,398,851 A | 3/1995 | Sancoff |
| 5,403,870 A | 4/1995 | Gross |
| 5,417,982 A | 5/1995 | Modi |
| 5,431,174 A | 7/1995 | Knute |
| 5,435,645 A | 7/1995 | Faccioli |
| 5,441,746 A | 8/1995 | Chagnon |
| 5,443,495 A | 8/1995 | Buscemi |
| 5,456,693 A | 10/1995 | Conston |
| 5,468,801 A | 11/1995 | Antonelli |
| 5,469,854 A | 11/1995 | Unger |
| 5,472,441 A * | 12/1995 | Edwards et al. ............ 606/41 |
| 5,476,472 A | 12/1995 | Dormandy |
| 5,484,584 A | 1/1996 | Wallace |
| 5,490,984 A | 2/1996 | Freed |
| 5,494,682 A | 2/1996 | Cohen |

(56) References Cited

U.S. PATENT DOCUMENTS

| | | |
|---|---|---|
| 5,494,940 A | 2/1996 | Unger |
| 5,512,604 A | 4/1996 | Demopolis |
| 5,514,090 A | 5/1996 | Kriesel |
| 5,525,334 A | 6/1996 | Ito |
| 5,534,589 A | 7/1996 | Hager |
| 5,541,031 A | 7/1996 | Yamashita |
| 5,542,935 A | 8/1996 | Unger |
| 5,553,741 A | 9/1996 | Sancoff |
| 5,556,610 A | 9/1996 | Yan |
| 5,556,931 A | 9/1996 | Imura |
| 5,558,255 A | 9/1996 | Sancoff |
| 5,558,822 A | 9/1996 | Gitman |
| 5,558,856 A | 9/1996 | Klaveness |
| 5,559,266 A | 9/1996 | Klaveness |
| 5,567,415 A | 10/1996 | Porter |
| 5,569,193 A | 10/1996 | Hofstetter |
| 5,569,449 A | 10/1996 | Klaveness |
| 5,569,468 A | 10/1996 | Modi |
| 5,571,182 A | 11/1996 | Ersek |
| 5,580,575 A | 12/1996 | Unger |
| 5,583,162 A | 12/1996 | Li |
| 5,585,112 A | 12/1996 | Unger |
| 5,595,821 A | 1/1997 | Hager |
| 5,622,657 A | 4/1997 | Takada |
| 5,624,685 A | 4/1997 | Takahashi |
| 5,635,215 A | 6/1997 | Boschetti |
| 5,637,087 A | 6/1997 | O'Neil |
| 5,639,710 A | 6/1997 | Lo |
| 5,648,095 A | 7/1997 | Illum |
| 5,648,100 A | 7/1997 | Boschetti |
| 5,650,116 A | 7/1997 | Thompson |
| 5,651,990 A | 7/1997 | Takada |
| 5,653,922 A | 8/1997 | Li |
| 5,657,756 A | 8/1997 | Vrba |
| 5,681,576 A | 10/1997 | Henry |
| 5,695,480 A | 12/1997 | Evans |
| 5,695,740 A | 12/1997 | Porter |
| 5,698,271 A | 12/1997 | Liberti |
| 5,701,899 A | 12/1997 | Porter |
| 5,715,824 A | 2/1998 | Unger |
| 5,716,981 A | 2/1998 | Hunter |
| 5,718,884 A | 2/1998 | Klaveness |
| 5,723,269 A | 3/1998 | Akagi |
| 5,725,522 A * | 3/1998 | Sinofsky ................. 606/8 |
| 5,725,534 A | 3/1998 | Rasmussen |
| 5,733,925 A | 3/1998 | Kunz |
| 5,741,331 A | 4/1998 | Pinchuk |
| 5,746,734 A | 5/1998 | Dormandy |
| 5,752,974 A | 5/1998 | Rhee |
| 5,756,127 A | 5/1998 | Grisoni |
| 5,760,097 A | 6/1998 | Li |
| 5,766,147 A | 6/1998 | Sancoff |
| 5,770,222 A | 6/1998 | Unger |
| 5,779,668 A | 7/1998 | Grabenkort |
| 5,785,642 A | 7/1998 | Wallace |
| 5,785,682 A | 7/1998 | Grabenkort |
| 5,792,478 A | 8/1998 | Lawin |
| 5,795,562 A | 8/1998 | Klaveness |
| 5,797,953 A | 8/1998 | Tekulve |
| 5,807,323 A | 9/1998 | Kriesel |
| 5,813,411 A | 9/1998 | Van Bladel |
| 5,823,198 A | 10/1998 | Jones |
| 5,827,502 A | 10/1998 | Klaveness |
| 5,827,531 A | 10/1998 | Morrison |
| 5,830,178 A | 11/1998 | Jones |
| 5,833,361 A | 11/1998 | Funk |
| 5,840,387 A | 11/1998 | Berlowitz-Tarrant |
| 5,846,518 A | 12/1998 | Yan |
| 5,853,752 A | 12/1998 | Unger |
| 5,855,615 A | 1/1999 | Bley |
| 5,863,957 A | 1/1999 | Li |
| 5,876,372 A | 3/1999 | Grabenkort |
| 5,877,224 A | 3/1999 | Brocchini |
| 5,885,216 A | 3/1999 | Evans |
| 5,885,547 A | 3/1999 | Gray |
| 5,888,546 A | 3/1999 | Ji |
| 5,888,930 A | 3/1999 | Smith |
| 5,891,155 A | 4/1999 | Irie |
| 5,894,022 A | 4/1999 | Ji |
| 5,895,398 A | 4/1999 | Wensel |
| 5,895,411 A | 4/1999 | Irie |
| 5,899,877 A | 5/1999 | Leibitzki |
| 5,902,832 A | 5/1999 | Van Bladel |
| 5,902,834 A | 5/1999 | Porrvik |
| 5,922,025 A | 7/1999 | Hubbard |
| 5,922,304 A | 7/1999 | Unger |
| 5,928,626 A | 7/1999 | Klaveness |
| 5,935,553 A | 8/1999 | Unger |
| 5,951,160 A | 9/1999 | Ronk |
| 5,957,848 A | 9/1999 | Sutton |
| 5,959,073 A | 9/1999 | Schlameus |
| 6,003,566 A | 12/1999 | Thibault |
| 6,015,546 A | 1/2000 | Sutton |
| 6,027,472 A | 2/2000 | Kriesel |
| 6,028,066 A | 2/2000 | Unger |
| 6,047,861 A | 4/2000 | Vidal |
| 6,048,908 A | 4/2000 | Kitagawa |
| 6,051,247 A | 4/2000 | Hench |
| 6,056,721 A | 5/2000 | Shulze |
| 6,056,844 A | 5/2000 | Guiles |
| 6,059,766 A | 5/2000 | Greff |
| 6,063,068 A | 5/2000 | Fowles |
| 6,071,495 A | 6/2000 | Unger |
| 6,071,497 A | 6/2000 | Steiner |
| 6,073,759 A | 6/2000 | Lamborne |
| 6,090,925 A | 7/2000 | Woiszwillo |
| 6,096,344 A | 8/2000 | Liu |
| 6,099,864 A | 8/2000 | Morrison |
| 6,100,306 A | 8/2000 | Li |
| 6,139,963 A | 10/2000 | Fujii |
| 6,149,623 A | 11/2000 | Reynolds |
| 6,160,084 A | 12/2000 | Langer |
| 6,162,377 A | 12/2000 | Ghosh |
| 6,165,193 A | 12/2000 | Greene |
| 6,167,313 A | 12/2000 | Gray |
| 6,179,817 B1 | 1/2001 | Zhong |
| 6,191,193 B1 | 2/2001 | Lee |
| 6,214,331 B1 | 4/2001 | Vanderhoff |
| 6,214,384 B1 | 4/2001 | Pallado |
| 6,224,630 B1 | 5/2001 | Bao |
| 6,224,794 B1 | 5/2001 | Amsden |
| 6,235,224 B1 | 5/2001 | Mathiowitz |
| 6,238,403 B1 | 5/2001 | Greene |
| 6,245,090 B1 | 6/2001 | Gilson |
| 6,251,661 B1 | 6/2001 | Urabe |
| 6,258,338 B1 | 7/2001 | Gray |
| 6,261,585 B1 | 7/2001 | Sefton |
| 6,264,861 B1 | 7/2001 | Tavernier |
| 6,267,154 B1 | 7/2001 | Felicelli |
| 6,268,053 B1 | 7/2001 | Woiszwillo |
| 6,277,392 B1 | 8/2001 | Klein |
| 6,280,457 B1 | 8/2001 | Wallace |
| 6,291,605 B1 | 9/2001 | Freeman |
| 6,296,604 B1 | 10/2001 | Garibaldi |
| 6,296,622 B1 | 10/2001 | Kurz |
| 6,296,632 B1 | 10/2001 | Luscher |
| 6,306,418 B1 | 10/2001 | Bley |
| 6,306,419 B1 | 10/2001 | Vachon |
| 6,306,425 B1 | 10/2001 | Tice |
| 6,306,427 B1 | 10/2001 | Annonier |
| 6,312,407 B1 | 11/2001 | Zadno-Azizi |
| 6,312,942 B1 | 11/2001 | Pluss-Wenzinger |
| 6,315,709 B1 | 11/2001 | Garibaldi |
| 6,335,384 B1 | 1/2002 | Evans |
| 6,344,182 B1 | 2/2002 | Sutton |
| 6,355,275 B1 | 3/2002 | Klein |
| 6,368,658 B1 | 4/2002 | Schwarz |
| 6,379,373 B1 | 4/2002 | Sawhney |
| 6,388,043 B1 | 5/2002 | Langer |
| 6,394,965 B1 | 5/2002 | Klein |
| 6,410,508 B1 | 6/2002 | Isales |
| 6,423,332 B1 | 7/2002 | Huxel |
| 6,432,437 B1 | 8/2002 | Hubbard |
| 6,436,112 B2 | 8/2002 | Wensel |

(56) References Cited

U.S. PATENT DOCUMENTS

| | | |
|---|---|---|
| 6,443,941 B1 | 9/2002 | Slepian |
| 6,458,296 B1 | 10/2002 | Heinzen |
| 6,476,069 B2 | 11/2002 | Krall |
| 6,495,155 B1 | 12/2002 | Tice |
| 6,544,503 B1 | 4/2003 | Vanderhoff |
| 6,544,544 B2 | 4/2003 | Hunter |
| 6,545,097 B2 | 4/2003 | Pinchuk |
| 6,547,794 B2 | 4/2003 | Auge, II |
| 6,565,887 B1 | 5/2003 | Gray |
| 6,575,896 B2 | 6/2003 | Silverman |
| 6,586,364 B2 | 7/2003 | Kubota |
| 6,602,261 B2 | 8/2003 | Greene |
| 6,602,524 B2 | 8/2003 | Batich |
| 6,605,111 B2 | 8/2003 | Bose |
| 6,629,947 B1 | 10/2003 | Sahatjian |
| 6,632,531 B2 | 10/2003 | Blankenship |
| 6,652,883 B2 | 11/2003 | Goupil |
| 6,680,046 B1 | 1/2004 | Boschetti |
| 6,699,222 B1 | 3/2004 | Jones |
| 6,706,394 B2 | 3/2004 | Kuehnle |
| 6,899,723 B2 | 5/2005 | Chen |
| 7,218,962 B2 | 5/2007 | Freyman |
| 7,727,555 B2 | 6/2010 | DiCarlo |
| 7,858,183 B2 | 12/2010 | Anderson |
| 7,963,287 B2 | 6/2011 | Lanphere et al. |
| 8,430,105 B2 * | 4/2013 | Lanphere et al. ............ 128/898 |
| 2001/0016210 A1 | 8/2001 | Mathiowitz |
| 2001/0036451 A1 | 11/2001 | Goupil |
| 2001/0051670 A1 | 12/2001 | Goupil |
| 2002/0054912 A1 | 5/2002 | Kim |
| 2002/0061954 A1 | 5/2002 | Davis |
| 2002/0160109 A1 | 10/2002 | Yeo |
| 2002/0182190 A1 | 12/2002 | Naimark |
| 2002/0197208 A1 | 12/2002 | Ruys |
| 2003/0007928 A1 | 1/2003 | Gray |
| 2003/0032935 A1 | 2/2003 | Damiano |
| 2003/0108614 A1 | 6/2003 | Volkonsky |
| 2003/0163187 A1 | 8/2003 | Weber |
| 2003/0183962 A1 | 10/2003 | Buiser |
| 2003/0185895 A1 | 10/2003 | Lanphere |
| 2003/0185896 A1 | 10/2003 | Buiser |
| 2003/0187320 A1 | 10/2003 | Freyman |
| 2003/0194390 A1 | 10/2003 | Krall |
| 2003/0203985 A1 | 10/2003 | Baldwin |
| 2003/0206864 A1 | 11/2003 | Mangin |
| 2003/0215519 A1 | 11/2003 | Schwarz |
| 2003/0233150 A1 | 12/2003 | Bourne |
| 2004/0076582 A1 | 4/2004 | Dimatteo |
| 2004/0091543 A1 | 5/2004 | Bell |
| 2004/0092883 A1 | 5/2004 | Casey, II |
| 2004/0096662 A1 | 5/2004 | Lanphere |
| 2004/0101564 A1 | 5/2004 | Rioux |
| 2004/0186377 A1 | 9/2004 | Zhong |
| 2005/0025800 A1 | 2/2005 | Tan |
| 2005/0037047 A1 | 2/2005 | Song |
| 2005/0095428 A1 | 5/2005 | Dicarlo |
| 2005/0129775 A1 | 6/2005 | Lanphere |
| 2005/0196449 A1 | 9/2005 | Dicarlo |
| 2005/0226935 A1 | 10/2005 | Kamath |
| 2005/0238870 A1 | 10/2005 | Buiser |
| 2005/0263916 A1 | 12/2005 | Lanphere |
| 2006/0045900 A1 | 3/2006 | Richard |
| 2006/0116711 A1 | 6/2006 | Elliott |
| 2007/0110786 A1 | 5/2007 | Tenney |

FOREIGN PATENT DOCUMENTS

| | | |
|---|---|---|
| DE | 4201461 | 7/1993 |
| DE | 94148686 | 12/1994 |
| DE | 29724255 | 10/2000 |
| DE | 10026620 | 3/2002 |
| EP | 0067459 | 12/1982 |
| EP | 0122624 | 10/1984 |
| EP | 0123235 | 10/1984 |
| EP | 0243165 | 10/1987 |
| EP | 0294206 | 12/1988 |
| EP | 0402031 | 12/1990 |
| EP | 0422258 | 4/1991 |
| EP | 0458079 | 11/1991 |
| EP | 0458745 | 11/1991 |
| EP | 0470569 | 2/1992 |
| EP | 0547530 | 6/1993 |
| EP | 0600529 | 6/1994 |
| EP | 0623012 | 11/1994 |
| EP | 07063760 | 4/1996 |
| EP | 0730847 | 9/1996 |
| EP | 0744940 | 12/1996 |
| EP | 0764047 | 3/1997 |
| EP | 0797988 | 10/1997 |
| EP | 0993337 | 4/2000 |
| ES | 2096521 | 3/1997 |
| JP | 59196738 | 11/1984 |
| JP | 62045637 | 2/1987 |
| JP | 4074117 | 3/1992 |
| JP | 6057012 | 3/1994 |
| JP | 9110678 | 4/1997 |
| JP | 9112823 | 5/1997 |
| JP | 9165328 | 6/1997 |
| JP | 9316271 | 12/1997 |
| JP | 10130329 | 5/1998 |
| JP | 2000189511 | 7/2000 |
| JP | 2001079011 | 3/2001 |
| JP | 2002017848 | 1/2002 |
| NZ | 255409 | 2/1997 |
| NZ | 517377 | 8/2003 |
| TW | 421658 | 2/2001 |
| WO | 9112823 | 9/1991 |
| WO | 9221327 | 12/1992 |
| WO | 9300063 | 1/1993 |
| WO | 9319702 | 10/1993 |
| WO | 9410936 | 5/1994 |
| WO | 9503036 | 2/1995 |
| WO | 9522318 | 8/1995 |
| WO | 9533553 | 12/1995 |
| WO | 9637165 | 11/1996 |
| WO | 9639464 | 12/1996 |
| WO | 9804616 | 2/1998 |
| WO | 9810798 | 3/1998 |
| WO | 9826737 | 6/1998 |
| WO | 9847532 | 10/1998 |
| WO | 9900187 | 1/1999 |
| WO | 9912577 | 3/1999 |
| WO | 9943380 | 9/1999 |
| WO | 9951278 | 10/1999 |
| WO | 9957176 | 11/1999 |
| WO | 0023054 | 4/2000 |
| WO | 0032112 | 6/2000 |
| WO | 0040259 | 7/2000 |
| WO | 0066183 | 11/2000 |
| WO | 0071196 | 11/2000 |
| WO | 0074633 | 12/2000 |
| WO | 0112359 | 2/2001 |
| WO | 0166016 | 9/2001 |
| WO | 0170291 | 9/2001 |
| WO | 0172281 | 10/2001 |
| WO | 0176845 | 10/2001 |
| WO | 0193920 | 12/2001 |
| WO | 0211696 | 2/2002 |
| WO | 0234298 | 5/2002 |
| WO | 0234299 | 5/2002 |
| WO | 0234300 | 5/2002 |
| WO | 0243580 | 6/2002 |
| WO | 03013552 | 2/2003 |
| WO | 03016364 | 2/2003 |
| WO | 03051451 | 6/2003 |
| WO | 03082359 | 10/2003 |
| WO | 2004019999 | 3/2004 |
| WO | 2004020042 | 3/2004 |
| WO | 2004040972 | 5/2004 |

(56) References Cited

FOREIGN PATENT DOCUMENTS

| | | |
|---|---|---|
| WO | 2004073688 | 9/2004 |
| WO | 2004075989 | 9/2004 |

OTHER PUBLICATIONS

"Injectable Tissue Implant Could Repair Ravages of Surgery", Clemson University, Biotech Week, Oct. 22, 2003, p. 117.
"Pulmonary artery pseudoaneurysm/aneurysm," http://www.mamc.amedd.army.mil/williams/chest/vascular/paaneurysm/paaneyrysm.htm, 2 pages.
"Smart Sutures Tie Themselves", Apr. 26, 2002, http://www.sciam.com/article.cfm?articleID=00047706-121F-1CDO-B4A8809EC588, 2 pages.
Abbara et al., "Transcervical Expulsion of a Fibroid as a Result of Uterine Artery Embolization for Leiomyomata", JVIR, vol. 10, No. 4, pp. 409-411, 1999.
Abrahams, J.M. et al., "Delivery of Human Vascular Endothelial Growth Factor with Platinum Coils Enhances Thickening and Coil Impregnation in a Rat Aneurysm Model", AJNR Am. J. Neuroradiol, 22:1410-1417, Aug. 2001.
Abrahams, J.M. et al., "Topic Review: Surface Modifications Enhancing Biological Activity of Guglielmi Detachable Coils in Treating Intracranial Aneurysms", Surg. Neurol. 54:34-41, 2000.
Ahuja, A.A., "Platinum Coil Coatings to Increase Thrombogenicity: A Preliminary Study in Rabbits", AJNR Am. J. Neuroradiol. 14:7994-798; Jul./Aug. 1993.
Antibody Labeling, http://www.altcorp.com/AffinityLabelinglablaeling.htm, pp. 1-6, May 20, 2003.
Bachtsi, A.R. et al., "An Experimental Investigation of Enzyme Release from Poly (vinyl alcohol) crosslinked Microspheres", J. Microencapsulation, vol. 12, No. 1, pp. 23-25; 1995.
Barr, J.D., et al., "Polyvinyl Alcohol Foam Particles Sizes and Concentrations Injectable through Microcatheters", JVIR, vol. 9, No. 1, pp. 113-118; 1998.
Barton, P. et al., "Embolization of Bone Metastases," Journal of Vascular and Interventional Radiology, 7(1):81-88 (Jan.-Feb. 1996).
Battinelli, L. et al., "New Class of Poly(vinyl alcohol) Polymrs as Column-Chromatography Stationary Phases for Candida Rugosa Lipase Isoforms Separation", J. Chromatogr A, vol. 753, No. 1, pp. 47-55; 1996.
Beaujeux, R. et al., "Trisacryl Gelatin Microspheres for Therapeutic Embolization, II: Preliminary Clinical Evaluation in Tumors and Arteriovenous Malformations," AJNR Am. I Neuroradiol., 17:541-548, Mar. 1996.
Berenstein, A. et al., "Catheter and Material Selection for Transarterial Embolization: Technical Considerations.", Radiology, vol. 132, No. 3, pp. 631-639; 1979.
Berenstein, A. et al., "Microembolization Techniques of Vascular Occlusion: Radiologic, Pathologic, and Clinical Correlation", AJNR Am I Neuroradiol, vol. 2, No. 3, pp. 261-267; 1981.
Berkowitz, R.P. et al., "Vaginal Expulsion of Submucosal Fibroids After Uterine Artery Embolization", Journal of Reproductive Medicine, vol. 44, No. 4, pp. 373-376; Apr. 1999, http://www.reproductivemedicine.com.
Bourke et al., "Protein Drug Release from Photocrosslinked Poly(vinyl alcohol) Hydrogels," Society for Biomaterials 28th Annual Meeting Transactions, p. 144 (2002).
Bradley, E.A. et al., "Transcatheter Uterine Artery Embolisation to Treat Large Uterine Fibroids", British Journal of Obstetrics and Gynaecology, vol. 105, pp. 235-240; Feb. 1998.
Brockmann, J. et al., "Radiolabeling of p-Bz-DOTA-CD-1 lc antibody with HY : Conjugation, Labeling Biodistribution studies", 2 pages, 2000 http://www.kernchemie.unl-mainz.de/downloads/jb2000/b14 brockmann.pdf.
Bruix, J. et al., "Transarterial Embolization Versus Symptomatic Treatment in Patients with Advanced Hepatocellular Carcinoma: Results of a Randomized, Controlled Trial in a Single Institution", Hepatology, Jun. 1998, vol. 27, No. 6, pp. 1578-1583, http://www.hepatitiscentral.com/hcv/hcc/embolization/references.html.

Buhle, Jr. EL, "Re: Re: Hepatic Arterial Embolization", UCLA Medicine Online, Mar. 10, 1996, http://www.meds.com/archive/mol-cancer/1996/msg00128.html, 2 pages.
Burczak, et al., "Long-term in vivo perfomance and biocompatibility of poly (vinyl alcohol) hydrogel macrocapsules for hybrid-type artificial pancreas", Biomaterials, vol. 17, No. 24, pp. 2351-2356, 1996.
Burczak, et al., "Polymeric materials for biomedical purposes obtained by radiation methods. V. hybrid artificial pancreas", Polim Med, vol. 24, No. 1-2, pp. 45-55, 1994 (Summary).
Capozza et al., "Endoscopic treatment of vesico-ureteric reflux and urinary incontinence: technical problems in the paediatric patient," British Journal of Urology, 75(4):538-542 (Apr. 1995).
Carroll, B.A. et al., "Gelatin Encapsulated Nitrogen Microbubbles as Ultrasonic Contrast Agents", Journal of Clinical and Laboratory Research, vol. 15, No. 1, pp. 260-266, Feb. 1980.
Carroll, B.A. et al., "Microbubbles as Ultrasonic Contrast Agents", Investigative Radiology, vol. 14, No. 3, p. 374, Supplement to May-Jun. 1979.
Carstensen, E.L. et al., "Determination of the Acoustic Properties of Blood and its Components", Journal of Acoustical Society of America, vol. 25, No. 2, pp. 286-289, Mar. 1953.
Choe, et al., "An experimental study of embolic affect according to infusion rate and concentration of suspension in transarterial particulate embolization", Invest Radiol, vol. 32, No. 5, pp. 260-270, 1997.
Chuang et al., "Experimental Canine Hepatic Artery Embolization with Polyvinyl Alcohol Foam Particles", Departments of Diagnostic Radiology and Veterinary Medicine, The University of Texas, M.D. Anderson Hospital and Tumor Institute at Houston, Texas, pp. 21-25, Oct. 1982.
Cirkel, U. et al., "Experience with Leuprorelin Acetate Depot in the Treatment of Fibroids: A German Multicentre Study", Clinical Therapeutics, vol. 14, Suppl. A, 1992.
Clarian Health Methodist Indiana Lions Gamma Knife Center, "Arteriovenous Malformation," http://www.clarian.com/tyhealth/gammaknife/cond arter.asp. 4 pages, Last Updated on Mar. 20, 2000.
Colombo M, "Treatment of Hepatocelluar Carcinoma", Journal of Viral Hepatitis, 4 (Suppl. 1):125-130 (1997), http://home.texoma.net/moreland/stats/hoc-9.html.
Concentric Medical, Inc.—Product Information (3 pages), 2002.
Cruise et al., "In Vitro and In Vivo Characterization of Hydrogel-Based Aneurysm Embolization System," Society for Biomaterials 28th Annual Meeting Transactions, p. 203 (2002).
de Gast, A.N. et al., "Transforming Growth Factor $^2$-coated Platinum Coils for Endovascular Treatment of Aneurysms: An Animal Study", Neurosurgery, vol. 49, No. 3, pp. 690-696, Sep. 2001.
Deasy, P. B., "Microencapsulation and Related Drug Processes", New York, NY, Marcel Dekker, Inc., 345 pages, 1984 (Table of Contents only).
Derdeyn, et al., "Collagen-coated acrylic microspheres for embolotherapy: in vivo and in vitro characteristics", American Journal of Neuroradiology, vol. 18, No. 4, pp. 647-653, 1997.
Derdeyn, et al., "Polyvinyl alcohol particle size and suspension characteristics", American Journal of Neuroradiology. vol. 16, pp. 1335-1343, 1995.
DiLuccio et al., "Sustained-Release Oral Delivery of Theophylline by Use of Polyvinyl Alcohol and Polyvinyl Alcohol-Methyl Acrylate Polymers", Journal of Pharmaceutical Sciences, vol. 83, No. 1, pp. 104-105, Jan. 1994.
Duckwiler et al., "Catheters, embolic agents spark neurointervention," Diagnostic Imaging, 16(5):66-72 (May 1994).
Ersek et al., "Bioplastique: A New Textured Copolymer Microparticle Promises Permanence in Soft-Tissue Augmentation," Plastic Reconstructive Surgery, 87(4):693-702 (Apr. 1991).
Eskridge, "Interventional Neuroradiology," Radiology, 172:991-1006 (Nov. 1989).
Feldman, L. et al., "Transcatheter Vessel Occlusion: Angiographic Results Versus Clinical Successl", Radiology, vol. 147, pp. 1-5, Apr. 1983.
Ferrofluids, Physical Properties and Applications Ferrofluidics Corp., Nashua, NH, 5 pages, 1986.
FeRx Incorporated, FERX Profile http://www.biotechshares.com/FERX.htm, 4 pages (Retrieved from the internet on Jun. 26, 2003).

(56) References Cited

OTHER PUBLICATIONS

Fritzsch, T. et al., "SH U 508, A Transpulmonary Echocontrast Agent", Investigative Radiology, vol. 25, Supplement 1, pp. S160-S161, Sep. 1990.
Fujimoto, S. et al., "Biodegradable Mitomycin C Microspheres Given Intra-Arterially for Inoperable Hepatic Cancer", Cancer, vol. 56, pp. 2404-2410, 1985.
Gander, et al., "Effect of polymeric network structure on drug release from cross-linked poly(vinyl alcohol) micromatrices", Pharm Res. vol. 6, No. 7, p. 578-584.
Germano, et al., "Histopathological follow-up study of 66 cerebral arteriovenous malformations after therapeutic embolization with polyvinyl alcohol", J Neurosurg, vol. 76, No. 4, pp. 607-614, 1992.
Geschwind et al., "Chemoembolization of Liver Tumor in a Rabbit Model: Assessment of Tumor Cell Death with Diffusion-Weighted MR Imaging and Histologic Analysis", Journal of Vascular and Interventional Radiology. vol. 11, No. 10, pp. 1244-1255, Dec. 2000.
Gilbert, W.M. et al., "Angiographic Embolization in the Management of Hemorrhagic Complications of Pregnancy", American Journal of Obstetrics and Gynecology, vol. 166, No. 2, pp. 493-497, Feb. 1992.
Gohel, et al., "Formulation design and optimization of modified-release microspheres of diclofenac sodium", Drug Dev Ind Pharm, vol. 25, No. 2, pp. 247-251, 1999.
Goldberg, B.B., "Ultrasonic Cholangiography", Radiology, vol. 118, pp. 401-404, Feb. 1976.
Goodwin, et al., "Overview of embolic agents and their indications", Eleventh Annual International Symposium on Endovascular Therapy, pp. 303-306. 1999.
Goodwin, et al., "Preliminary experience with uterine artery embolization for uterine fibroids", Journal of Vascular and Interventional Radiology, vol. 8, No. 4. pp. 517-526, 1997.
Gramiak, R. et al., "Ultrasound Cardiography: Contrast Studies in Anatomy and Function", Radiology, vol. 92, No. 5, pp. 939-948, Apr. 1969.
Gramiak et al., "Echocardiography of the Aortic Root," Investigative Radiology, 3(5):356-366 (Sep.-Oct. 1968).
Grandfils, et al., "Preparation of poly (D,L) lactide microspheres by emulsion solvent evaporation, and their clinical implications as a convenient embolic material", J Biomed Mater Res, vol. 26, No. 4, pp. 467-479, 1992.
Greenwood, L.H. et al., "Obstetric and Nonmalignant Gynecologic Bleeding: Treatment with Angiographic Embolization", Radiology, vol. 164, No. 1, pp. 155-159, Jul. 1987.
Gupta et al., "Plasma-induced graft polymerization of acrylic acid onto poly(ethylene terephthalate) films: characterization and human smooth muscle cell growth on grafted films," Biomaterials, 23:863-871 (2002).
Halstenberg et al., "Biologically Engineered Protein-graft-Poly(ethylene glycol) Hydrogels: A Cell Adhesive and Plasmin-Degradable Biosynthetic Material for Tissue Repair," Biomacromolecules, 3(4):710-723 (2002).
Hamada et al., "Embolization with Cellulose Porous Beads, II: Clinical Trial," AJNR Am. J. Neuroradiol., 17:1901-1906 (Nov. 1996).
Hirano et al., "Transcutaneous Intrafold Injection for Unilateral Vocal Fold Paralysis: Functional Results," Ann. Otol. Rhinol Laryngol., 99(8):598-604 (Aug. 1990).
Horak et al., "Hydrogels in endovascular embolization. I. Spherical particles of poly (2-hydroxyethyl methacrylate) and their medicobiological properties", Biomaterials, 7(3):188-192 (May 1986).
Horak et al., "Hydrogels in endovascular embolization. II. Clinical use of spherical particles", Biomaterials, 7(6):467-470 (Nov. 1986).
Huang, et al., "Percutaneous endovascular embolization of intracerebral arteriovenous malformations. Experience in 72 cases", Chin Med J, vol. 108, No. 6, pp. 413-419, 1995.
Jack, et al., "Radiolabeled polyvinyl alcohol particles: a potential agent to monitor embolization procedures", Int J Rad Appl Instrum B, vol. 13, No. 3, pp. 235-243, 1986.
Jiaqi, Y. et al., "A New Embolic Material: Super Absorbent Polymer (SAP) Microsphere and Its Embolic Effects,"Nippon Acta Radiologica, 56:19-24 (1996) (Abstract).
Jones, S.K. et al., "Experimental Examination of a Targeted Hyperthermia System Using Inductively Heated Ferromagnetic Micrspheres in Rabbit Kidney", Phys. Med. Biol., vol. 46, No. 2, pp. 385398. Feb. 2001, www.iop.org/Journals/pb.
Joy C, et al., "Use of Preoperative Embolization in the Treatment of Vascular Metastatic Lesions of the Spine," http://www.aaos.org/wordhtml/anmeet9l/scipro/ppr472.htm, Mar. 12, 1991.
Jung et al., "Sulfobutylated poly(vinyl alcohol)-graft-poly(lactide-co-glycolide)s facilitate the preparation of small negatively charged biodegradable nanospheres," Journal of Controlled Release, 67:157-169 (2000).
Kai, et al., "The utility of the microcrystalline cellulose sphere as a particulate embolic agent: an experimental study", American Journal of Radiology, vol. 21, No. 6, pp. 1160-1163, 2000.
Kallmes, D.F. et al., "In Vitro Proliferation and Adhesion of Basic Fibroblast Growth Factor-producing Fibroblasts on Platinum Coils", Radiology, vol. 206, No. 1, pp. 237-243, Jan. 1998.
Kan, et al., "In vivo microscopy of the liver after injection of lipiodol into the hepatic artery and portal vein in the rat", Acta Radiologica, vol. 30, pp. 419-425, 1989.
Kerber, "Flow-Controlled Therapeutic Embolization: A Physiologic and Safe Technique", AJR, vol. 134, pp. 557-561, Mar. 1980.
Kerber, C., "Balloon Catheter with a Calibrated Leak", Radiology, vol. 120, pp. 547-550, Sep. 1976.
Kerber et al., "Polyvinyl Alcohol Foam: Prepackaged Emboli for Therapeutic Embolization", American Journal Roentgenol, vol. 130, pp. 1193-1194, Jun. 1978.
Khankan et al., "Embolic Effects of Superabsorbent Polymer Microspheres in Rabbit Renal Model: Comparison with Tris-acryl Gelatin Microspheres and Polyvinyl Alcohol," Radiation Medicine, 22(6):384-390 (2004).
Kim, et al., "Composite poly(vinyl alcohol) beads for controlled drug delivery", Pharm Res, vol. 9, No. 1, pp. 10-16, 1992.
Kim et al., "Hollow Silica Spheres of Controlled Size and Porosity by Sol-Gel Processing," J. Am. Ceram. Soc., 74(8):1987-1992 (Aug. 1991).
Kim et al., "Poly(vinyl alcohol) beads with core-shell structure for drug delivery" Cosmetic and Pharmaceutical Applications of Polymers, Plenum Press, New York, pp. 209-214 (1991).
Kim et al., "Suspension polymerized poly(vinyl alcohol) beads for drug delivery," Polymeric Materials: Science and Engineering, Proceedings of the ACS Division of Polymeric Materials: Science and Engineering, 63:64-67 (1990).
Kochan, J.P. et al., "Interventional Neuroradiology: Current Practices and Techniques at Temple University Hospital," http://www.temple.edu/radiology/stroke.html, 5 pages.
Krinick et al., "A polymeric drug delivery system for the simultaneous delivery of drugs activatable by enzymes and/or light," J. Biomater. Sci. Polymer Edn, 5(4):303-324 (1994).
Kuhn, R. et al., "Embolic Occlusion of the Blood Supply to Uterine Myomas: Report of 2 Cases", Aust. NZ. J. Obstet. Gynaecol., vol. 39, No. 1. pp. 120-122, Feb. 1999.
Kurata, et al., "Preoperative embolization for meningiomas using PVA particles", No Shinkei Geka, vol. 20, No. 4, pp. 367-373, 1992 (Abstract).
Kurbatova, G.T. et al., "Magnetically-guided Anesthetics Based on Highly Dispersed Iron Powders Coated by Polyacrylamide", Biofizika, vol. 47, No. 2, pp. 331-337, Mar.-Apr. 2002 http://intapp.medscape.com/px/medlineapp (Abstract).
Kurosaki et al., "Evaluation of PVA-Gel Spheres as GI-Transit Time Controlling Oral Drug Delivery System", Proceedings of the 19th International Symposium on Controlled Release of Bioactive Materials, Orlando, Florida, pp. 273-274, Jul. 26-31, 1992.
Kusano et al., "Low-dose particulate polyvinylalcohol embolization in massive small artery intestinal hemorrahage. Experimental and clinical results", Invest Radiol, vol. 22, No. 5, pp. 388-392, 1982.
Labarre et al., "Complement activation by substituted polyacrylamide hydrogels for embolisation and implantation", Biomaterials, vol. 23, pp. 2319-2327, 2002.
Lammer, et al., "Transcatheteral embolization with polyvinyl alcohol-technic and experimental investigations", Rontgenblatter, vol. 36, No. 1, pp. 10-14, 1983 (Abstract).

(56) References Cited

OTHER PUBLICATIONS

Latchaw et al., "Polyvinyl Foam Embolization of Vascular and Neoplastic Lesions of the Head, Neck, and Spine", Radiology, vol. 131, pp. 669-679, Jun. 1979.
Laurent, "Materials and biomaterials for interventional radiology," Biomed. & Pharmacother., 52:76-88 (1998).
Lemperle et al., "PMMA Microspheres for Intradermal Implantation: Part I. Animal Research," Annals of Plastic Surgery, 26(1):56-63 (Jan. 1991).
Lendlein, A. et al., "Biodegradable, Elastic Shape-Memory Polymers for Potential Biomedical Applications", Science, vol. 296, pp. 1673-1676, May 31, 2002.
Leung et al., "Determinants of Postembolization Syndrome after Hepatic Chemoembolization", Journal of Vascular and Interventional Radiology, vol. 12, No. 3, pp. 320-326, Mar. 2001.
Leventon, William, "Hemocompatible Coatings for Blood-Contacting Devices", Medical Device & Diagnostic Industry: Coating Technologies—New Methods to Ensure Blood Compatibility, vol. 25, No. 8, pp. 62-67, Aug. 2003.
Levy et al., "Transcatheter Uterine Artery Embolization for the Treatment of Symptomatic Uterine Fibroid Tumors,"—Journal of Women's Imaging, 2(4):168-175 (2000).
Lipman, "Uterine artery embolization for the treatment of symptomatic uterine fibroids: A review," Applied Radiology, 29(7):15-20 (Jul. 2000).
Lowery, C.L. et al., "Screeneing Tests for Intrauterine Growth Retardation: A Comparison of Umbilical Artery Doppler to Real-Time Ultrasound", Echocardiography, vol. 7, No. 2, pp. 159-164, Mar. 1990.
Marich, K.W. et al., "Real-Time Imaging with a New Ultrasonic Camera: Part I, In Vitro Experimental Studies on Transmission Imaging of Biological Structures", Journal of Clinical Ultrasound, vol. 3, No. 1, pp. 5-16, Mar. 1975.
Markoff, et al., "Uterine arteriovenous malformation successfully embolized with a liquid polymer, , isobutyl 2-cyanoacrylate", Am. J. Obstet. Gynecol., 155:659-660 (Sep. 1986).
Markus et al., "Experimental Aspects of High-Intensity Transient Signals in the Detection of Emboli," J. Clin. Ultrasound., 23(2):81-87 (Feb. 1995).
Maruhashi, "Modified Polyvinyl Alcohols I and II," Polyvinyl Alcohol—Developments John Wiley & Sons, Chichester, England, pp. 160-161 and pp. 186-191 (1992).
Marx, W.F. et al., "Endovascular Treatment of Experimental Aneurysms by Use of Biologically Modified Embolic Devices: Coil-mediated Intraaneurysmal Delivery of Fibroblast Tissue Allografts", AJNR. AM. J. Neuroradiol., vol. 22, pp. 323-333, Feb. 2001.
Mather, P.T., Research Group Homepage, Basic Goals and Methods, http://www.ims.uconn.edu/-mather, 4 pages.
Matsumaru, et al., "Embolic materials for endovascular treatment of cerebral lesions", J Biomater Sci Polym Ed, vol. 8, No. 7, pp. 555-569, 1997.
Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", Neurosurgery, vol. 53, No. 2, pp. 402-408, Aug. 2003.
Matsumoto, Y. et al., "Room-Temperature Ferromagnetism in Transparent Transition Metal-Doped Titanium Dioxide", Science, vol. 291, pp. 854-856, Feb. 2, 2001 www.sciencemag.org.
Mavligit, G. et al., "Gastrointestinal Leiomyosarcoma Metastatic to the Liver," Cancer, 75(8):2083-2088 (Apr. 15, 1995).
McIvor, J. et al., "Pregnancy After Uterine Artery Embolization to Control Haemorrhage from Gestational Trophoblastic Tumour", British Journal of Radiology, vol. 69, No. 823, pp. 624-629, Jul. 1996.
MerocelXL Sponge with Hytrol http://www.xomed.cominewproducts/merocelxl/merocelxl_earwick.asp, 3 pages, 2001.
Mid-American Interventional Radiological Society, "New Treatment for Uterine Fibroids Avoids Surgery," http://www.mirs.org/fibroids.htm, 6 pages, Submitted in Oct. 1999.
Moroz, P. et al., "Arterial Embolization Hyperthermia in Porcine Renal Tissue", Journal of Surgical Research, vol. 105, No. 2, pp. 209-214, Jun. 15, 2002.
Moroz, P. et al., "Hepatic Clearance of Arterially Infused Ferromagnetic Particles", Int. J.
Nakabayashi, et al., "Evaluation of particulate embolic materials with MR imaging, scanning electron microscopy, and phase-contrast microscopy", American Journal of Neuroradiology, vol. 18, No. 3, pp. 485-491, 1997.
Nakstad, et al., "Embolization of intracranial arteriovenous malformations and fistulas with polyvinyl alcohol particles and platinum fibre coils", Neuroradiology, vol. 34, No. 4, pp. 348-351, 1992.
Namiki, "Application of Teflon Paste for Urinary Incontinence—Report of 2 Cases," Uro. Int., 39:280-282 (1984).
Nash, et al., "Modifications of polyslyrenic matrices for the purification of proteins. II. Effect of the degree of glutaraldehyde-poly(vinyl alcohol) crosslinking on various dye ligand chromatography systems", J Chromatogr A, vol. 776, No. 1, pp. 55-63, 1997.
Nikishin LF et al., "Interventional radiology in diffuse toxic goiter", European Congress of Radiology, Abstract 9041, 1999, http://www.ecr.org/conferences/ecr1999/sciprg/abs/p090041.htm, 7 pages.
Ophir, et al., "Ultrasonic backscatter from contrast producing collagen microspheres", Ultrasonic Imaging, vol. 2, pp. 67-77, 1980.
Oregon Health Sciences University, "Fibroid Embolization," http://www.uhmc.edu/dotter-fibroid, 34 pages.
Orienti et al., "Crosslinked Polyvinylalcohol Hydrogels as Vehicles for Hydrophilic Drugs," Arch. Pharm. Pharm. Med. Chem., 333:421-424 (2000).
Orsini, L. F. et al., "Pelvic Organs in Premenarcheal Girls: Real-Time Ultrasonography", Radiology, vol. 153, No. 1, pp. 113-116, Oct. 1984.
Parker, et al., "A particulate contrast agent with potential for ultrasound imaging of liver", Ultrasound in Medicine and Biology, vol. 13, No. 9, pp. 555-566, 1987.
Pedley et al., "Hydrogels in Biomedical Applications," British Polymer Journal, 12:99-110 (Sep. 1980).
Pesant A.C. et al., "Dural fistulas involving the cavernous sinus: Treatment by embolization—7 cases", European Congress of Radiology, Abstract 3-088. 1997, http://www.ecr.org/conferences/ecr1997/sciprg/abs/9703088p.htm, 1 page.
Phillips, D. R. et al., "Experience with Laparoscopic Leiomyoma Coagulation and Concomitant Operative Hysteroscopy", J. Am. Assoc. Gynecol. Laparosc, vol. 4, No. 4, pp. 425-533,—Aug. 1997.
Physicians' Desk Reference Family Guide to Women's Health, "Chapter 7—Common Disorders of the Reproductive System," http://www.healthsquare.com/pdrfewhichapters/which01.htm, 24 pages.
Pistel et al., "Brush-like branched biodegradable polyesters, part III Protein release from microspheres of poly(vinyl alcohol)-graft-poly(D,L-lactic-co-glycolic acid)," Journal of Controlled Release, 73:7-20 (2001).
Politano et al., "Periurethral Teflon Injection for Urinary Incontinence," The Journal of Urology, 111:1801183 (1974).
Poppe, W. et al., "Pregnancy after Transcatheter Embolization of a Uterine Arteriovenous Malformation", Am. I Obstet. Gynecol., vol. 156, No. 5, pp. 1179-1180, May 1987.
Pritchard, et al., "Poly(Vinyl Alcohol): Basic Properties and Uses", London, England: Gordon and Breach Science Publishers, pp. 95-97, 1970.
Progelhof et al., "Table 4.21. Properties of electrical insulating films (101)," Polymer Engineering Principles: Properties, Processes, and Tests for Design, Hanser Publishers, Munich, p. 383 (1993).
Pryor J. and Berenstein A., "Epistaxis (Nose-bleeds)." http://www.wehealny.org/inn/Radiology/nosebleeds.html, 1 page.
Purdy, et al., "Arteriovenous malformations of the brain: choosing embolic materials to enhance safety and ease of excision", J Neurosurg, vol. 77, No. 2, pp. 217-222, 1992.
PVA Plus, AngioDynamics Inc., "Reliable PVA Foam Formulated for Consistency and Controlled Delivery Embolization Particles Ordering Information," www.angiodynamics.com, 2 pages (Aug. 2002).
Quisling, et al., "Histopathology analysis of intraarterial polyvinyl alcohol microemboli in rat cerebral cortex", American Journal of Neuroradiology, vol. 5, pp. 101-104, 1984.

(56) References Cited

OTHER PUBLICATIONS

Rajan et al., "Sarcomas Metastatic to the Liver: Response and Survival after Cisplatin. Doxorubicin, Mitomycin-C, Ethiodol, and Polyvinyl Alcohol Chemoembolization", Journal of Vascular and Interventional Radiology, vol. 12, No. 2, pp. 187-198, Feb. 2001.
Ramos, et al., "Tumor vascular signals in renal masses: detection with Doppler US", Radiology, vol. 168, No. 3, pp. 633-637, 1988.
Ravina, J.H. et al., "Advantage of Pre-Operative Embolization of Fibroids: About a Multicentric Set of 31 Cases", Contracept. Fertil. Sex., vol. 23, No. 1, pp. 45-49, Jan. 1995 (abstract).
Ravina, J.H. et al., "Arterial Embolisation to Treat Uterine Myomata", Lancet, vol. 346, pp. 671-674, Sep. 9, 1995.
Ravina, J.H. et al., "Interest of Particulate Arterial Embolization in the Treatment of Some Uterine Myoma", Bull. Acad. Natle. Med., vol. 181, No. 2, pp. 233-246, Feb. 4, 1997 (Summary).
Repa, I. et al., "Mortalities Associated with Use of a Commercial Suspension of Polyvinyl Alcohol," Radiology, 170(2):395-399 (Feb. 1989).
Rhine et al., "Polymers for Sustained Macromolecule Release: Procedures to Fabricate Reproducible Delivery Systems and Control Release Kinetics," Journal of Pharmaceutical Sciences, 69(3):265-270 (Mar. 1980).
Rump, A. et al., "Pharmacokinetics of Intraarterial Mitomycin C in the Chemoembolisation Treatment of Liver Metastases," Gen. Pharmac., 27(4):669-671 (1996).
Schetky, "Shape-Memory Alloys," Encyclopedia of Chemical Technology, Third Edition, vol. 20, John Wiley & Sons, New York, pp. 726-736 (1982).
Schlief, R. et al., "Enhanced Color Doppler Echocardiography of the Left Heart After Intravenous Injection of a New Saccharide Based Agent in Humans", Circulation, vol. 82, No. 2, p. 28, Oct. 1990 (Abstract).
Schlief, R. et al., "Successful Opacification of the Left Heart Chamber on Echocardiographic Examination after Intravenous Injection of a New Saccharide Based Contrast Agent", Echocardiography, vol. 7, No. 1, pp. 61-64, Jan. 1990.
Schwarz et al., "The acoustic filter: An ultrasonic blood filter for the heart-lung machine," J. Thorac. Cardiovasc. Surg., 104(6):1647-1653 (Dec. 1992).
Shafik, "Intraesophageal Polytef injection for the treatment of reflux esophagitis," Surg. Endosc., 10:329-331 (1996).
Shape Shifters, http://www.sciam.com/tehbiz/050lscicit6.html, 3 pages, 2001.
Shung, K.K. et al., "Scattering of Ultrasound by Blood", IEEE Transactions on Biomedical Engineering, vol. BME-23, No. 6, pp. 460-467, Nov. 1976.
Sigelmann, R.A. et al., "Analysis and Measurement of Ultrasound Backscattering from an Ensemble of Scatters Excited by Sine-Wave Bursts", Journal of Acoustical Society of America, vol. 53, No. 4, pp. 1351-1355, Apr. 1973.
SIR-Spheres, Radioactive Implant (Yttrium-90 Microspheres), Sirex Medical, Inc., San Diego, CA, Nov. 6, 2000, pp. 1-15.
SIR-Spheres (Yttrium-90 Microspheres), pp. 1-12.
Sirtex Medical Limited Product Description http://www.sirtex.comnp=72, 3 pages (Retrieved from the internet on May 27, 2003).
Sirtex Medical Limited Targeted Radiotherapy with SIR-Spheres http://www.sirtex.comnp=57, 2 pages (Retrieved from the internet on May 27, 2003).
Siskin et al., "Pathologic Evaluation of a Spherical Polyvinyl Alcohol Embolic Agent in a Porcine Renal Model," J. Vasc. Interv. Radiol., 14:89-98 (2003).
Skotland, T. et al., "In Vitro Stability Analyses as a Model for Metabolism of Ferromagnetic Particles (ClariscanTm), a Contrast Agent for Magnetic Resonance Imaging", J. Pharm. Biomed. Anal., vol. 28, No. 2, pp. 323-329, Apr. 15, 2002.
Smith et al., "Evaluation of Polydimethylsiloxane as an alternative in the Endoscopic Treatment of Vesicoureteral Reflux," The Journal of Urology, 152:1221-1224 (Oct. 1994).
Smith et al., "Left Heart Opacificiation with Peripheral Venous Injection of a New Saccharide Echo Contrast Agent in Dogs", JACC, vol. 13, No. 7, pp. 1622-1628, Jun. 1989.
Soppimath et al., "Controlled release of antihypertensive drug from the interpenetrating network poly(vinyl alcohol)-guar gum hydrogel microspheres," J Biomater. Sci. Polymer Edn, 11(1):27-43 (2000).
Spickler, et al., "The MR appearance of endovascular embolic agents in vitro with clinical correlation", Comput Med Imaging Graph, vol. 14, No. 6, pp. 415-423, 1990.
Spies JB, "Georgetown University Medical Center. Uterine Fibroid Embolization (UFE). An alternative to surgery for patients with uterine fibroids. Literature Review," http://www.fibroidcutions.com/pr-lit.htm, 6 pages, Sep. 1, 2001.
Stancato-Pasik, A. et al., "Obstetric Embolotherapy: Effect on Menses and Pregnancy", Radiology, vol. 204, No. 3, pp. 791-793, Sep. 1997.
Stein, R. et al., "Targeting Human Cancer Xenografts with Monoclonal Antibodies Labeled Using Radioiodinated, Diethylenetriaminepentaacetic Acid-appended Peptides", Clinical Cancer Research, vol. 5, No. 10, pp. 3079-3087, Oct. 1999 (Supplement).
Strasnick et al., "Transcutaneous Teflon Injection for Unilateral Vocal Cord Paralysis: An Update," The Laryngoscope. 101:785-787 (Jul. 1991).
Stridbeck, H. et al, "Collateral Circulation Following Repeated Distal Embolization of the Hepatic Artery in Pigs," Invest. Radiol., 19(3):179-183 (1984).
Strunk, et al., "Treatment of congenital coronary arteriovenous malformations with microparticle embolization", Cathet Cardiovasc Diagn, vol. 22, No. 2, pp. 133-136, 1991.
Swanson DA et al., "The role of embolization and nephrectomy in the treatment of metastatic renal carcinoma", Urologic Clinics of North America, 7(3):719-730, 1980, University of Pennsylvania Cancer Center—Oncolink, http://www.oncolink.upenn.edu/pdg_html/cites/00/00585.html.
Tabata et al., "Tumor accumulation of poly(vinyl alcohol) of different sizes after intravenous injection", Journal of Controlled Release, vol. 50, pp. 132-133, Jan. 2, 1998.
Tadavarthy et al., "Polyvinyl Alcohol (Ivalon)—A New Embolic Material", The American Journal of Roentgenology Radium Therapy and Nuclear Medicine, vol. 125, No. 3, pp. 609-616, Nov. 1975.
Tadavarthy et al., "Polyvinyl Alcohol (Ivalon) as an Embolizing Agent", Seminars in Interventional Radiology, vol. 1, No. 2, pp. 101-109, Jun. 1984.
Tamatani, S. et al., "Histological Interaction of Cultured Endothelial Cells and Endovascular Embolic Materials Coated with Extracellular Matrix", J. Neurosurg., vol. 86, No. 1, pp. 109-112, Jan. 1997.
Tao, et al., "Study of microspheres for embolization of hepatic artery", (Translation) Acta Pharmaceutica Sinica, vol. 23, No. 1, pp. 55-60, 1988.
Terada, et al., "Preoperative embolization of meningiomas fed by ophthalmic branch arteries", Surg Neurol, vol. 45, No. 2, pp. 161-166, 1996.
Thanoo, B. C. et al., "Preparation and Properties of Barium Sulphate and Methyl Iothalamate Loaded Poly(vinyl Alcohol) Microspheres as Radiopaque Particulate Emboli," Journal of Applied Biomaterials,2:67-72(1991).
Thanoo, et al., "Controlled release of oral drugs from cross-linked polyvinyl alcohol microspheres", J Pharm Pharmacol, vol. 45, No. 1, pp. 16-20, 1993.
Thanoo, et al., "Tantalum loaded silicone microspheres as particulate emboli", J Microencapsul, vol. 8, No. 1, pp. 95-101, 1991.
The Fibroid Embolization Center of the New York United Hospital Medical Center, "Fibroid Facts," http://www.uhmc.com/fibro2.htm, 9 pages.
The Vanderbilt-Ingram Cancer Center, "Kidney Cancer," http://www.mc.Vanderbilt.Edu/cancer/cancerinfo/kidney.html, 1 page, 2001.
Thelen, V.M. et al., "Catheter Embolisation of Metastasising Renal Carcinomas Using Butyle-2-cyano-acrylate", Fortschr. Rontgenstr., vol. 124, No. 3, pp. 232-235, Mar. 1976 (Abstract).

(56) References Cited

OTHER PUBLICATIONS

Tian et al., "Design and synthesis of amphiphilic poly (ethylene glycol) derivatives as micellar drug delivery systems," Polymer Preprints, 43(2):719-720 (Fall 2002).

Tikkakoski, et al., "Preoperative embolization in the management of neck paragangliomas", Laryngoscope, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using microcatheterwith special reference to serial xylocaine tests and intravascular pressure monitoring", Surgical Neurology, vol. 42, No. 2, pp. 148-156, 1994.

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variococele and its treatment," http://www.hsc.sunysb.edu/urology/male_inf...variocoele_and_its_treatment.html, 8 pages, Last Updated on Mar. 12, 2001.

Vivas S et al., "Fistula arterioportal γ hemobilia en ur paciente con traspiante hepatico", Gastroenterol Hepatol, 21(2):88-89, http://www.doyma.es/copiani/revistas/gastro/abstr/abs_p080.html, Feb. 1998 (Abstract).

Vogel F, "Nonsurgical Management of Uterine Fibroids," http://www.holyname.org/brochure/fibroids.html, 5 pages.

Wakhloo, et al., "Extended preoperative polyvinyl alcohol microembolizatoin of intracranial meningiomas: Assessment of two embolization techniques", American Journal of Neuroradiology, vol. 14, pp. 571-582, 1993.

Walker WJ, "Non Surgical Treatment of Fibroids in the UK by Uterine Artery Embolisation an Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastrointestinal Hemorrhage," J. Gastrointest. Surg., 3:61-66 (1999).

Waltman, A.C. et al., "Technique for Left Gastric Artery Catheterization", Radiology, vol. 109, No. 3, pp. 732-734, Dec. 1973.

White, Jr., "Embolotherapy in Vascular Disease," American Journal of Roentgenology, 142:27-30—(JaritiaTy 1984).

Widder, K. et al., "Magnetic Microspheres: Synthesis of a Novel Parenteral Drug Carrier", Journal of Pharmaceutical Sciences, vol. 68, No. 1, pp. 79-82, Jan. 1979.

Widder, K.J. et al., "Selective Targeting of Magnetic Microspheres Containing Adriamycin: Total Remision in Yoshida Sarcoma-Bearing Rats", Proceedings of the 16th Annual Meeting of American Society of Clinical Oncology, May 16-17, 1980, San Diego, CA, p. 261.

Wikholm G et al., "Embolization of Cerebral Arteriovenous Malformations: Part I Technique, Morphology, and Complications", Neurosurgery, 39(3):448-459 (Sep. 1996).

Winters et al., "Periurethral injection of collagen in the treatment of intrinsic sphincteric deficiency in the female patient," The Urologic Clinics of North American, 22(3):673-678 (Aug. 1995).

Worthington-Kirsch, et al., "Uterine arterial embolization for the management of leiomyomas: Quality-of-life assessment and clinical response", Radiology, vol. 208, No. 3, 625-629, 1998.

Worthington-Kirsch RL, "Interventionalists offer management option for uterine fibroids," Diagnostic Imaging, 21(3):47-49, Mar. 1999, http://www.dimag.com/references/9903wortrefs.html.

Wright, K.C. et al., "Partial Splenic Embolization Using Polyvinyl Alcohol Foam, Dextran, Polystyrene, or Silicon," Radiology, 142:351-354, Feb. 1982.

Wu, A.M., "Engineered Antibodies for Breast Cancer Imaging and Therapy," http://www.cbcrp.org/research/PageGrant.asp?grant_id=111, 3 pages. 1996.

Yamada, T. et al., "Extended Intraarterial Cisplatin Infusion for Treatment of Gynecologic Cancer After Altercation of Intrapelvic Blood Flow and Implantation of a Vascular Access Device", Cardiovasc. Intervene. Radiol., vol. 19, pp. 139-145, 1996.

Yamashita, Y. et al., "Transcatheter Arterial Embolization of Obstetric and Gynaecological Bleeding: Efficacy and Clinical Outcome", British Journal of Radiology, vol. 67, pp. 530-534, Jun. 1994.

Yoon et al., "Surface Immobilization of Galactose onto Aliphatic Biodegradable Polymers for Hepatocyte Culture," Biotechnol. Bioeng., 78(1):1-10 (Apr. 5, 2002).

Yusi et al., "Submucosal Injection of Polyvinyl Alcohol in Artificially Created Vesico-Ureteral Reflux: A Preliminary Report," Asian J. Surg., 18(2):122-127 (Apr. 1995).

Zisch et al., "Covalently conjugated VEGF-fibrin matrices for endothelialization," Journal of Controlled Release,72:101-113 (2001).

Ziskin, M.C. et al., "Contrast Agents for Diagnostic Ultrasound", Investigative Radiology, vol. 7, No. 6, pp. 500-505, Nov.-Dec. 1972.

Zou, Ying-hua, et al., 'Experimental Canine Hapatic Artery Embolization with Polyvinyl Alcohol Microspheres,' Zhong Hua Fang-She Xue ZaZhi, 23(6):330-332 (1989).

* cited by examiner

TISSUE-TREATMENT METHODS

CROSS-REFERENCE TO RELATED APPLICATIONS

This application is a continuation of U.S. application Ser. No. 13/106,563, filed on May 12, 2011, and issued as U.S. Pat. No. 8,430,105 on Apr. 30, 2013, which is a continuation of U.S. application Ser. No. 11/117,156, filed on Apr. 28, 2005, and issued as U.S. Pat. No. 7,963,287 on Jun. 21, 2011, the entire contents of each of these are incorporated herein by reference.

TECHNICAL FIELD

This invention relates to tissue-treatment methods.

BACKGROUND

Energy, such as RF energy, can be employed to degrade unhealthy or unwanted tissue, such as a wart, a mole, a cyst, scar tissue, and/or a tumor. In some cases, for example, an RF probe can be delivered into the unhealthy or unwanted tissue via a catheter. Once positioned within the tumor, RF-emitting tines can be deployed and activated. Upon activation, the tines can emit RF energy to degrade the tissue by, for example, heating the tissue.

SUMMARY

The invention relates to polymer insulators and methods of using the same.

In one aspect, the invention features a method that includes separating a first portion of tissue of a subject from a second portion of tissue of the subject so that there is a space between the first and second portions of tissue. The method also includes disposing a material between the first and second portions of tissue, and exposing the first portion of tissue to energy to treat the first portion of tissue. The material disposed between the first and second portions of tissue can be one or more of the following: deionized water; a buffered saline solution; liquid polymers; gels; particles; foams; and/or gases.

In another aspect, the invention features a method that includes disposing a material between a first portion of tissue of a subject and a second portion of tissue of the subject. The method also includes exposing the first portion of tissue to energy to treat the first portion of tissue. The second portion of tissue can be substantially unexposed to the energy while the first portion of tissue is exposed to the energy. The distance between the first and second portions of tissue is at most about five centimeters, and the material disposed between the first and second portions of tissue can be one or more of the following: deionized water; a buffered saline solution; liquid polymers; gels; particles; foams; and/or gases.

The methods can include one or more of the following features.

In some embodiments, the second portion of tissue is substantially unexposed to the energy while the first portion of tissue is exposed to the energy.

In certain embodiments, the energy includes RF energy, microwave energy, ultrasonic energy, laser energy, and/or heat. In some embodiments, exposing the first portion of tissue to energy includes cooling the first portion of tissue.

In some embodiments, the first portion of tissue includes unhealthy tissue (e.g., cancerous tissue), and/or the second portion of tissue includes healthy tissue. Examples of tissue include bodily vessel tissue, bladder tissue, bone tissue, brain tissue, breast tissue, bronchi tissue, diaphragm tissue, esophagus tissue, gall bladder tissue, heart tissue, intestine tissue, kidney tissue, larynx tissue, liver tissue, lung tissue, lymph vessel tissue, lymph node tissue, nerve tissue, ovary tissue, pancreas tissue, prostate tissue, skin tissue, stomach tissue, and thyroid tissue, trachea tissue, urethra tissue, ureter tissue, uterus tissue, and vertebral disc tissue.

In certain embodiments, the material is formed of particles. The particles can have, for example, a size of at most about 10,000 microns. The particles can include one or more polymeric materials. The particles can include a material having a dielectric constant of at least about 2.1 and/or a dielectric strength of at least about 100 Kv/mm in some embodiments.

In some embodiments, the material is a liquid polymer.

In certain embodiments, the material is a foam.

In some embodiments, the material is a gas. Examples of gases include air, helium, neon, argon, krypton, xenon, nitrogen, and carbon dioxide.

In some embodiments, the material is deionized water and/or a buffered saline solution.

In certain embodiments, the material is a water soluble polysaccharide and/or an ionically cross-linkable polymer.

In certain embodiments, the material is a ceramic material.

In some embodiments, the material is capable of undergoing an endothermic reaction.

In some embodiments, the space between the first and second portions of tissue is at most about five centimeters.

The methods can provide one or more of the following advantages.

In some embodiments, the methods can protect healthy or desired tissue from damage, while treating (e.g., ablating, degrading, destroying) unhealthy or undesired tissue.

In certain embodiments, the methods can allow relatively small regions of desired or healthy tissue to be protected while treating (e.g., ablating, degrading, destroying) undesired or unhealthy tissue.

In certain embodiments, the methods can protect regions of desired or healthy tissue that are difficult to access.

Features and advantages are in the description, drawings, and claims.

DESCRIPTION OF DRAWINGS

Like reference symbols in the drawings indicate like elements.

DETAILED DESCRIPTION

The methods include disposing one or more materials between a region of unhealthy tissue and a region of healthy tissue, and exposing the unhealthy tissue to energy (e.g., RF energy) to damage or destroy the unhealthy tissue. The materials can include one or more of the following: deionized water; a buffered saline solution; liquid polymers; gels; particles; foams; and/or gases. The material disposed between the unhealthy and healthy tissue regions can protect the healthy tissue so that it is substantially unharmed by the energy.

Figure 1A:
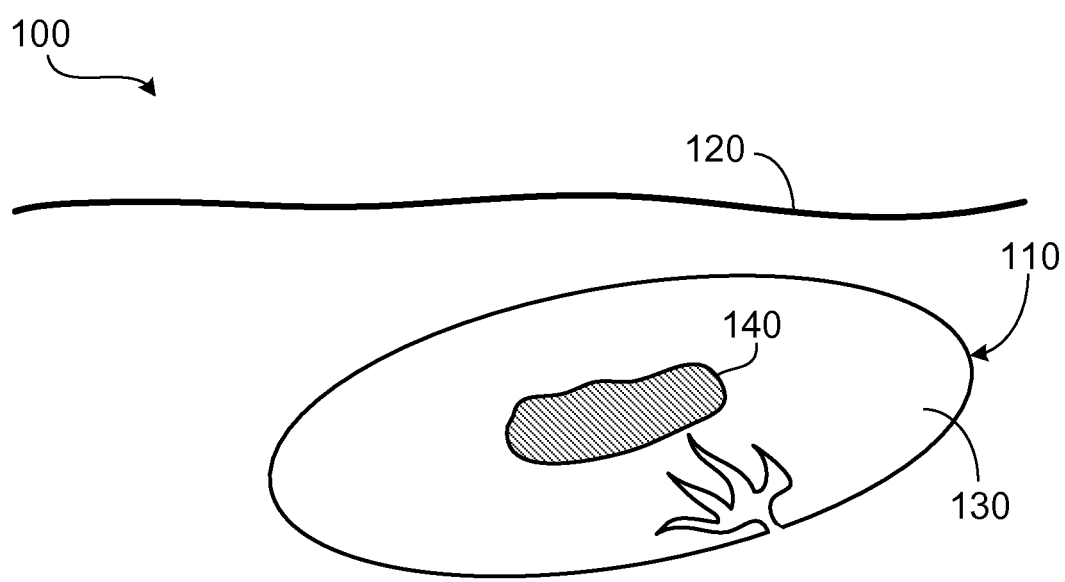
FIG. 1A is a cross-sectional view of a cancerous liver of a subject.

For example, FIG. 1A shows a portion 100 of a subject including a liver 110 and skin 120. Liver 110 includes healthy tissue 130 and unhealthy tissue 140 (e.g., a cancerous tissue, such as a cancerous tumor).

Figure 1B:
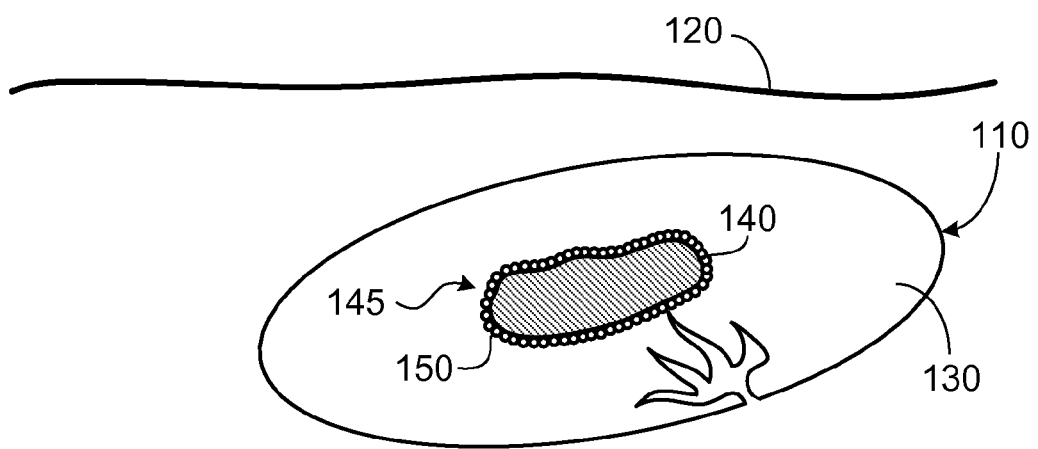
FIG. 1B is a cross-sectional view of the liver of FIG. 1A with a protective layer of particles disposed between the cancerous and non-cancerous tissue regions.

FIG. 1B shows healthy tissue 130 separated from unhealthy tissue 140 by a protective layer 145 of particles 150. As discussed in more detail below, particles 150 can protect healthy tissue 130 while unhealthy tissue 140 is treated with energy.

For example, particles 150 can be formed of a material that is a poor conductor of certain types of energy (e.g., RF energy) relative to tissues 130 and 140 of the subject. Thus, when inserted between healthy and unhealthy tissues 130, 140, particles 150 substantially prevent energy applied to unhealthy tissue 140 from harming healthy tissue 130. As a result, healthy tissue 130 is substantially protected from harm when energy is applied to unhealthy tissue 140.

In some embodiments, particles 150 are at least partially formed from one or more polymers. Examples of polymers include polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly (lactic-co-glycolic) acids (e.g., poly(d-lactic-co-glycolic) acids), polypropylene, polytetrafluorethylene, polyethyleneterephthalate, polycarbonate, polyphenyleneoxide, polysulfone, polyhydantoine, polyamide-imide, polyimide, cellulose triacetate, cellulose acetate butyrate, and copolymers or mixtures thereof.

Additional examples of materials from which particles 150 can be at least partially formed include alginates (e.g., sodium alginate), alginate salts, xanthan gums, natural gum, agar, agarose, chitosan, carrageenan, fucoidan, furcellaran, laminaran, hypnea, eucheuma, gum arabic, gum ghatti, gum karaya, gum tragacanth, hyaluronic acid, locust beam gum, arabinogalactan, pectin, amylopectin, other water soluble polysaccharides and other ionically cross-linkable polymers.

In some embodiments, particles 150 are at least partially formed of a bio-absorbable and/or bio-erodible material, such as a polysaccharide (such as an alginate); a polysaccharide derivative; a water soluble polymer (such as a polyvinyl alcohol, e.g., that has not been cross-linked); biodegradable poly DL-lactide-poly ethylene glycol (PELA); a hydrogel (e.g., polyacrylic acid, haluronic acid, gelatin, carboxymethyl cellulose); a polyethylene glycol (PEG); chitosan; a polyester (e.g., a polycaprolactone); a poly(lactic-acid) (PLA); a poly (lactic-co-glycolic) acid (e.g., a poly(d-lactic-co-glycolic) acid); or a combination thereof.

In certain embodiments, particles 150 are at least partially formed of one or more ceramic materials. In general, a ceramic material contains one or more metallic elements and one or more non-metallic elements. Examples of ceramics include metal oxides, such as aluminum oxide, cerium oxide, copper oxide, iron oxide, magnesium oxide, and potassium oxide.

In some embodiments, particles 150 can be formed of a glass. Examples of glasses include oxides of silicon, beryllium, boron, germanium, phosphorous, vanadium, lead, tin, zinc, zirconium, and titanium, as well as such nonoxide compounds as germanium sulphide, metal fluorides, and iodites. Other examples of glasses include certain metallic selenides, tellurides, arsenides, phosphides, and obsidian.

In certain embodiments, particles 150 contain encapsulated air (e.g., to enhance the protective ability of particles 150). In some embodiments, particles 150 contain an encapsulated composition capable of undergoing an endothermic reaction. For example, particles 150 can encapsulate a ammonium nitrate and water composition. Consequently, particles 150 can absorb greater amounts of energy (e.g., heat) in some cases.

In some embodiments, particles 150 are formed from a material that has a relatively high dielectric constant. For example, particles 150 can have a dielectric constant that is higher than the dielectric constant of tissues 130 and 140. This can, for example, allow protective layer 145 to be a relatively poor conductor of RF energy. For example, particles 150 can be formed of a material having a dielectric constant of at least about 2.0 (e.g., at least about 2.1, at least about 2.7, at least about 3.1). In some embodiments, particles 150 can be formed of a material having a dielectric constant of from about 2.0 to about 4.5 (e.g., from about 2.1 to about 4.5, from about 2.7 to about 4.5, from about 3.1 to about 4.5). The term dielectric constant, as used herein, is measured by ASTM D150 at 50 Hz and 20° C.

In some embodiments, the material from which particles 150 are made has a relatively high dielectric strength. For example, particles 150 can have a dielectric strength that is higher than the dielectric strength of tissues 130 and 140. This can, for example, allow layer 145 to be a relatively poor conductor of RF energy. For example, particles 150 can be formed of a material having a dielectric strength of at least about 100 kV/mm (e.g., at least about 200 kV/mm, at least about 240 kV/mm, at least about 280 kV/mm). In some embodiments, particles 150 can be formed of a material having a dielectric strength of from about 50 kV/mm to about 350 kV/mm (e.g., from about 100 kV/mm to about 300 kV/mm, from about 200 kV/mm to about 300 kV/mm, from about 240 kV/mm to about 300 kV/mm, from about 280 kV/mm to about 300 kV/mm). The term dielectric strength, as used herein, is measured by ASTM D149.

In certain embodiments, particles 150 can be formed of a material having a relatively high dissipation factor. For example, particles 150 can have a dissipation factor that is higher than the dissipation factor of tissues 130 and 140. This can, for example, allow layer 145 to be a relatively poor conductor of RF energy. For example, particles 150 can be formed of a material having a dissipation factor of at least about 0.2 (e.g., at least about 0.7, at least about 1.5, at least about nine, at least about 21). The term dissipation factor, as used herein, is measured by ASTM D150 at 50 Hz and 20° C.

In some embodiments, particles 150 can be formed of a material having a relatively high volume resistivity. For example, particles 150 can have a volume resistivity that is higher than the volume resistivity of tissues 130 and 140. This can, for example, allow layer 145 to be a relatively poor conductor of RF energy. For example, particles 150 can be formed of a material having a volume resistivity of at least about $10^6$ to about $10^{17}$ ohm-cm (e.g., at least about $10^{14}$ ohm-cm, at least about $10^{16}$ ohm-cm, at least about $10^{17}$ ohm-cm). As used herein, the volume resistivity of a particle is measured by ASTM D257-99.

In certain embodiments, particles 150 can be formed of a material having a relatively low surface resistivity. For example, particles 150 can have a surface resistivity that is lower than the surface resisitivity of tissues 130 and 140. For example, particles 150 can be formed of a material having a surface resistivity of at most about $10^{12}$ to about $10^{16}$ ohm-cm (e.g., at most about $10^{16}$ ohm-cm, at most about $10^{14}$ ohm-cm, at most about $10^{12}$ ohm-cm). The term surface resistivity, as used herein, is measured by ASTM D257-99.

In certain embodiments, the material from which particles 150 are made can be chosen based on the intensity and/or type of energy used to treat unhealthy tissue 140. As an example, in embodiments in which RF energy and/or microwave energy is used, it can be beneficial to use particles formed of a material with a higher dielectric constant and/or a higher dielectric strength. As an additional example, in embodiments in which ultrasonic energy is used, it can be beneficial to use particles formed of a material that can retard the transmission of ultrasonic energy therethrough. As another example, in embodiments in which laser energy is used, it can be beneficial to use particles formed of a material that is capable of absorbing and/or refracting laser energy.

In some embodiments, particles 150 have a diameter of no greater than about 10,000 microns (e.g., no greater than about 7,500 microns, no greater than about 5,000 microns, no greater than about 2,500 microns, no greater than about 2,000 microns, no greater than about 1,5000 microns, no greater than about 1,000 microns, no greater than about 500 microns, no greater than about 400 microns, no greater than about 300 microns, no greater than about 200 microns, no greater than about 100 microns). In some embodiments, particles 150 have a diameter of about 100 microns to about 10,000 microns (e.g., about 100 microns to about 1000 microns, about 100 microns to 500 microns, about 2,500 microns to about 5,000 microns, about 5,000 microns to about 10,000 microns, about 7,500 microns to about 10,000 microns).

Figure 1C:
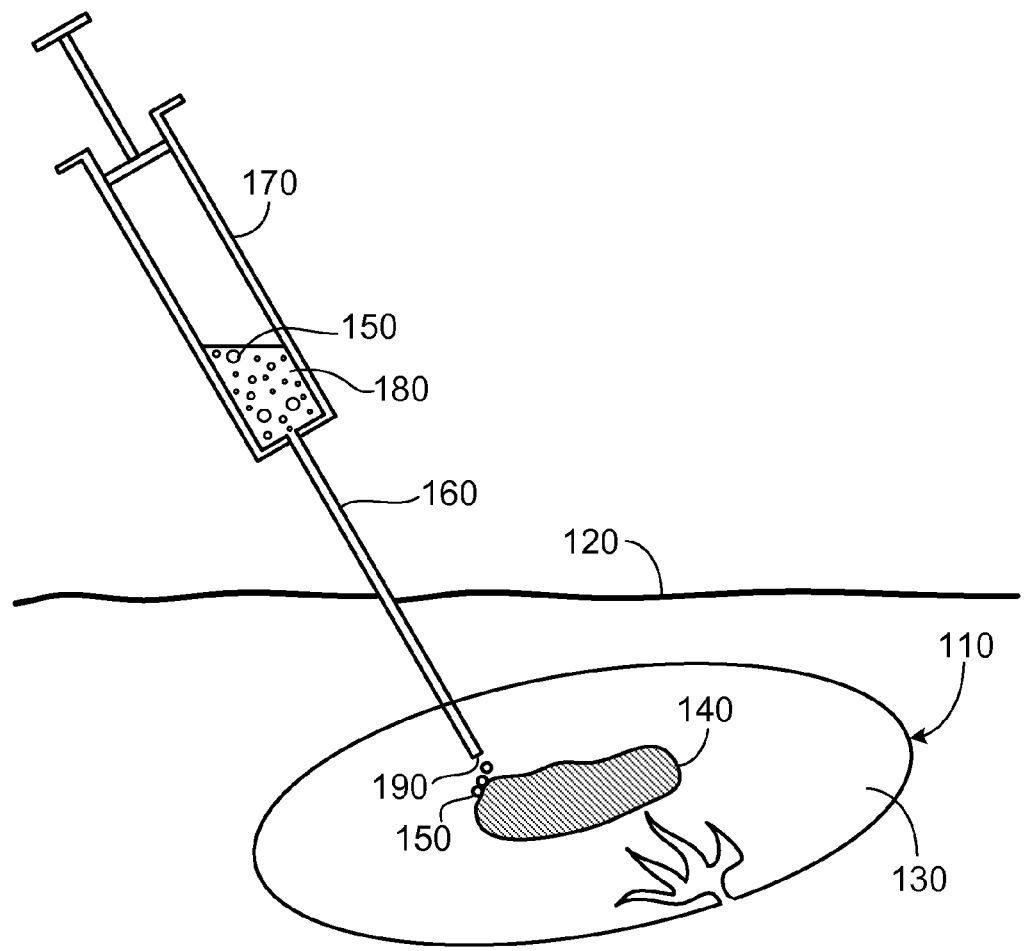
FIG. 1C illustrates administration of particles between cancerous and non-cancerous tissue regions of the liver of FIG. 1A.

FIG. 1C shows a method of disposing particles 150 between healthy tissue 130 and unhealthy tissue 140 using a needle 160. Needle 160 is in fluid communication with a syringe 170, which contains particles 150 suspended in a carrier fluid 180. An end 190 of needle 160 is inserted through skin 120 of the subject and into healthy tissue 130. Needle 160 is inserted until end 190 is positioned between healthy and unhealthy tissues 130, 140 in order to separate healthy tissue 130 from unhealthy tissue 140 and form a gap between healthy and unhealthy tissues 130, 140. Particles 150 and carrier fluid 180 are then injected from syringe 170 into the gap to form protective layer 145. In some embodiments, this process is repeated until protective layer 145 reaches a desired thickness. In certain embodiments, the method is performed so that protective layer 145 covers only a particular region or regions of unhealthy tissue 140. For example, any of various imaging modalities, such as ultrasound, CT, MRI, and/or fluoroscopy, can be used to help the user (e.g., a physician) to position needle 160 in a targeted region of the tissue. Consequently, particles 150 can be disposed (e.g., injected) substantially only in the targeted region. It may be unnecessary, for example, to completely separate healthy tissue 130 from unhealthy tissue 140 when only a particular region of healthy tissue 130 is exposed to energy emitted during a treatment. In such cases, particles 150 can be restricted to regions likely to be exposed to the energy.

Carrier fluid 180 can be a pharmaceutically acceptable carrier, such as a buffered saline solution, non-ionic contrast agent, therapeutic agent, or a combination of these carriers. In some embodiments, carrier fluid 180 includes deionized water, water for injection, liquid polymer, gel polymer, gas, or a combination of these carriers. Carrier fluid 180, in some cases, can contribute to the protection of healthy tissue 130. In certain embodiments, carrier fluid 180 includes one or more insulating materials, such as glass fibers. The insulating materials can enhance the ability of carrier fluid 180 to contribute to the protection of healthy tissue 130.

In some embodiments, particles 150 are not suspended in a carrier fluid. For example, particles 150 alone can be contained within syringe 170, and injected from syringe 170 into the gap between healthy tissue 130 and unhealthy tissue 140.

While embodiments have been described in which a needle is used to form the opening between healthy tissue 130 and unhealthy tissue 140, in some embodiments, other techniques can be used to form this opening. For example, the opening can be formed using an open procedure in which an incision is made in the subject to gain access to unhealthy tissue 140. As another example, blunt dissection techniques may be used to form the opening between healthy tissue 130 and unhealthy tissue 140. After forming the opening, healthy tissue 130 can be separated from unhealthy tissue 140 using any of various techniques. For example, a needle can be injected between healthy and unhealthy tissues 130, 140. As another example, one or more gases or liquids can be pumped into the region between healthy tissue 130 and unhealthy tissue 140. After separating healthy tissue 130 from unhealthy tissue 140, particles 150 can be implanted within a gap created between the separated healthy and unhealthy tissues 130, 140 using any of various techniques. For example, in some embodiments, particles 150 can be injected into the gap via a needle, directly from a syringe, or a catheter.

Figure 1D:
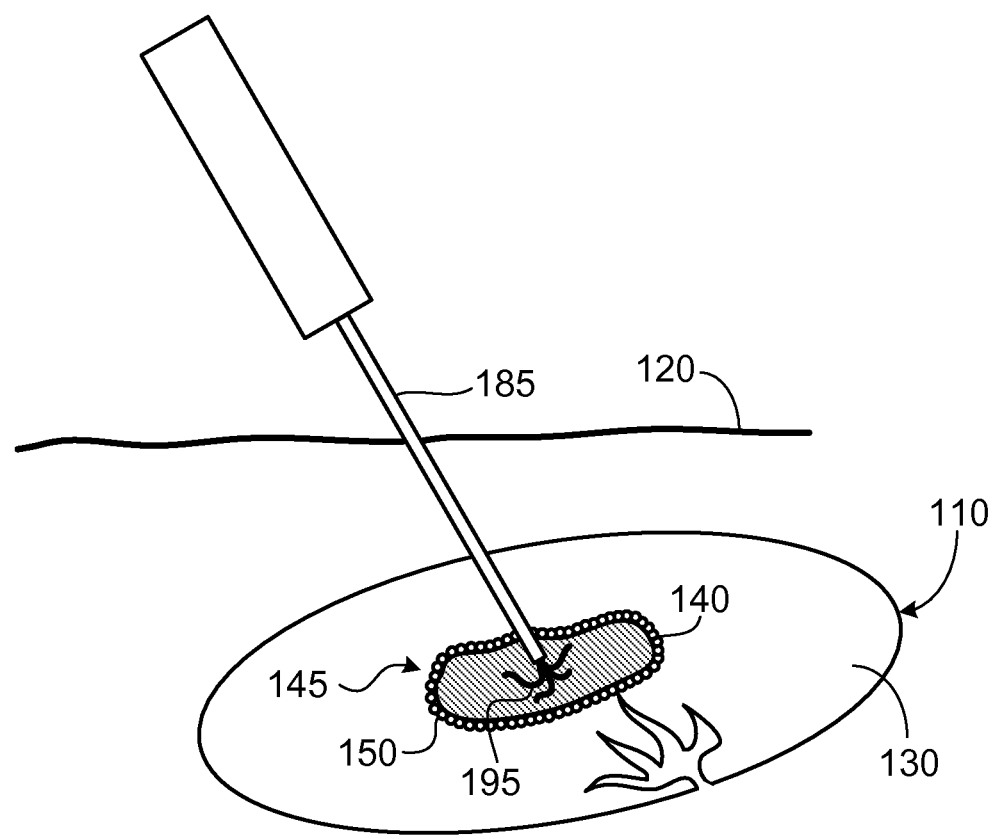
FIG. 1D illustrates emission of energy within the cancerous tissue region of the liver of FIGS. 1A, 1B, and 1C to degrade the cancerous tissue.

FIG. 1D illustrates a method of treating unhealthy tissue 140 with RF energy using an RF probe 185 (e.g., a 3.5 centimeter coaxial LeVeen electrode, available from Boston Scientific Corporation). Probe 185 is positioned within unhealthy tissue 140 (e.g., by insertion through skin 120 of the subject). Once positioned within unhealthy tissue 140, tines 195 of RF probe 185 are deployed within unhealthy tissue 140, and RF probe 185 is activated so that RF energy is emitted from tines 195. The RF energy emitted from tines 195 can heat unhealthy tissue 140 around tines 195 to treat (e.g., ablate, damage destroy) portions of unhealthy tissue 140 that are exposed to the energy.

Protective layer 145 substantially prevents the RF energy from penetrating healthy tissue 130 when unhealthy tissue 140 is exposed to the RF energy. For example, the RF energy is prevented from penetrating healthy tissue 130 with a substantially harmful intensity. Thus, the method can be used to treat unhealthy tissue 140 without substantially harming healthy tissue 130.

The level of protection provided by protective layer 145 of particles 150 can be a function of the thickness of protective layer 145. As an example, in some embodiments, as the thickness of protective layer 145 increases, its ability to conduct energy (e.g., heat and/or RF energy) can decrease, and, as the thickness of protective layer 145 decreases, its ability to conduct energy (e.g., heat and/or RF energy) can decrease. In such embodiments, it can become more difficult for energy to be transported from unhealthy tissue 140 to healthy tissue 130 via protective layer 145 as the thickness of protective layer 145 increases, and it can become easier for energy to be transported from unhealthy tissue 140 to healthy tissue 130 via protective layer 145 as the thickness of protective layer 145 decreases. Thus, it may be beneficial to increase the thickness of protective layer 145 as the intensity of the energy used to treat unhealthy tissue 140 increases, and to decrease the thickness of protective layer 145 as the intensity of energy decreases (e.g., to obtain a desired degree of insulation while keeping the space between unhealthy tissue 140 and healthy tissue 130 relatively small to decrease possible trauma to the subject).

The thickness of protective layer 145 can be modified using any of various techniques. For example, the thickness of protective layer 145 can be increased or decreased by increasing or decreasing the size of particles 150, and/or by disposing a greater or lesser number of particles across a thickness of the gap between healthy and unhealthy tissues 130, 140. In certain embodiments, multiple layers of particles 150 are disposed between healthy tissue 130 and unhealthy tissue 140 in order to increase the thickness of protective layer 145.

In some embodiments, after separating healthy tissue 130 from unhealthy tissue 140, the gap between healthy and unhealthy tissues 130, 140 can be at most about five centimeters (e.g., at most about four centimeters, at most about three centimeters, at most about two centimeters, at most about one centimeter, at most about 0.5 centimeter, at most about 0.25 centimeter, or at most about 0.1 centimeter). For example, protective layer 145 of particles 150 can have a thickness of at most about five centimeters (e.g., at most about four centimeters, at most about three centimeters, at most about two centimeters, at most about one centimeter, at most about 0.5 centimeter, at most about 0.25 centimeter, or at most about 0.1 centimeter). In some embodiments the gap between healthy and unhealthy tissues 130, 140 can be about 0.1 centimeter to about five centimeters (e.g., about 0.1 centimeter to about three centimeters, about 0.1 centimeter to about one centimeter, about 0.1 centimeter to about 0.5 centimeter, about 0.1 centimeter to about 0.25 centimeter). For example, protective layer 145 of particles 150 can have a thickness of about 0.1 centimeter to about five centimeters (e.g., about 0.1 centimeter to about three centimeters, about 0.1 centimeter to about one centimeter, about 0.1 centimeter to about 0.5 centimeter, about 0.1 centimeter to about 0.25 centimeter).

In certain embodiments, particles 150 include one or more therapeutic agents (e.g., drugs) that can be delivered to healthy and/or unhealthy tissues 130, 140. The therapeutic agent(s) can be in and/or on the particle. Therapeutic agents include agents that are negatively charged, positively charged, amphoteric, or neutral. Therapeutic agents include genetic therapeutic agents, non-genetic therapeutic agents, and cells, and can be negatively charged, positively charged, amphoteric, or neutral. Therapeutic agents can be, for example, materials that are biologically active to treat physiological conditions; pharmaceutically active compounds; gene therapies; nucleic acids with and without carrier vectors; oligonucleotides; gene/vector systems; DNA chimeras; compacting agents (e.g., DNA compacting agents); viruses; polymers; hyaluronic acid; proteins (e.g., enzymes such as ribozymes); immunologic species; nonsteroidal anti-inflammatory medications; oral contraceptives; progestins; gonadotrophin-releasing hormone agonists; chemotherapeutic agents; and radioactive species (e.g., radioisotopes, radioactive molecules). Non-limiting examples of therapeutic agents include anti-thrombogenic agents; antioxidants; angiogenic and anti-angiogenic agents and factors; anti-proliferative agents (e.g., agents capable of blocking smooth muscle cell proliferation); calcium entry blockers; and survival genes which protect against cell death.

Exemplary non-genetic therapeutic agents include: anti-thrombotic agents such as heparin, heparin derivatives, urokinase, and PPack (dextrophenylalanine proline arginine chloromethylketone); anti-inflammatory agents such as dexamethasone, prednisolone, corticosterone, budesonide, estrogen, sulfasalazine and mesalamine; antineoplastic/anti-proliferative/anti-mitotic agents such as paclitaxel, 5-fluorouracil, cisplatin, doxorubicin; vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anticoagulants such as D-Phe-Pro-Arg chloromethyl ketone, an RGD peptide-containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; and agents that interfere with endogenous vasoactive mechanisms.

Exemplary genetic therapeutic agents include: anti-sense DNA and RNA; DNA coding for: anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation, and the family of bone morphogenic proteins ("BMP's"), including BMP2, BMP3, BMP4, BMP5, BMP6 (Vgr1), BMP7 (OP1), BMP8, BMP9, BMP10, BM11, BMP12, BMP13, BMP14, BMP15, and BMP16. Currently preferred BMP's are any of BMP2, BMP3, BMP4, BMP5, BMP6 and BMP7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Vectors of interest for delivery of genetic therapeutic agents include: Plasmids, Viral vectors such as adenovirus (AV), adenoassociated virus (AAV) and lentivirus, Non-viral vectors such as lipids, liposomes and cationic lipids.

Cells include cells of human origin (autologous or allogeneic), including stem cells, or from an animal source (xenogeneic), which can be genetically engineered if desired to deliver proteins of interest.

Several of the above and numerous additional therapeutic agents appropriate for the practice of the present invention are disclosed in U.S. Pat. No. 5,733,925, which is incorporated herein by reference. Therapeutic agents disclosed in this patent include the following: "Cytostatic agents" (i.e., agents that prevent or delay cell division in proliferating cells, for example, by inhibiting replication of DNA or by inhibiting spindle fiber formation). Representative examples of cytostatic agents include modified toxins, methotrexate, adriamycin, radionuclides (e.g., such as disclosed in Fritzberg et al., U.S. Pat. No. 4,897,255), protein kinase inhibitors, including staurosporin, a protein kinase C inhibitor of the following formula:

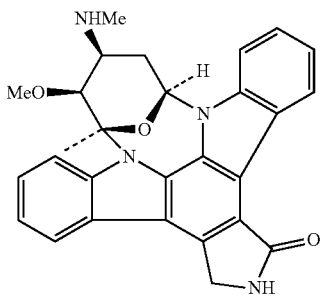 [SMILES: CN[C@H]1C[C@H]2O[C@@](C)([C@H]1OC)n1c3ccccc3c3c4c(c5c6ccccc6n2c5c31)C(=O)NC4]

as well as diindoloalkaloids having one of the following general structures:

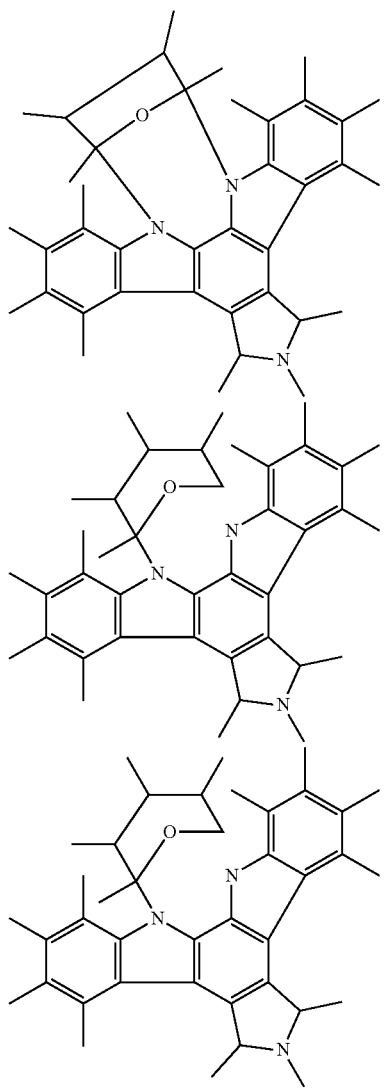

as well as stimulators of the production or activation of TGF-beta, including Tamoxifen and derivatives of functional equivalents (e.g., plasmin, heparin, compounds capable of reducing the level or inactivating the lipoprotein Lp(a) or the glycoprotein apolipoprotein(a)) thereof, TGF-beta or functional equivalents, derivatives or analogs thereof, suramin, nitric oxide releasing compounds (e.g., nitroglycerin) or analogs or functional equivalents thereof, paclitaxel or analogs thereof (e.g., taxotere), inhibitors of specific enzymes (such as the nuclear enzyme DNA topoisomerase II and DNA polymerase, RNA polymerase, adenyl guanyl cyclase), superoxide dismutase inhibitors, terminal deoxynucleotidyl-transferase, reverse transcriptase, antisense oligonucleotides that suppress smooth muscle cell proliferation and the like.

Other examples of "cytostatic agents" include peptidic or mimetic inhibitors (i.e., antagonists, agonists, or competitive or non-competitive inhibitors) of cellular factors that may (e.g., in the presence of extracellular matrix) trigger proliferation of smooth muscle cells or pericytes: e.g., cytokines (e.g., interleukins such as IL-1), growth factors (e.g., PDGF, TGF-alpha or -beta, tumor necrosis factor, smooth muscle- and endothelial-derived growth factors, i.e., endothelin, FGF), homing receptors (e.g., for platelets or leukocytes), and extracellular matrix receptors (e.g., integrins). Representative examples of useful therapeutic agents in this category of cytostatic agents addressing smooth muscle proliferation include: subfragments of heparin, triazolopyrimidine (trapidil; a PDGF antagonist), lovastatin, and prostaglandins E1 or I2.

Agents that inhibit the intracellular increase in cell volume (i.e., the tissue volume occupied by a cell) such as cytoskeletal inhibitors or metabolic inhibitors. Representative examples of cytoskeletal inhibitors include colchicine, vinblastin, cytochalasins, paclitaxel and the like, which act on microtubule and microfilament networks within a cell. Representative examples of metabolic inhibitors include staurosporin, trichothecenes, and modified diphtheria and ricin toxins, *Pseudomonas* exotoxin and the like. Trichothecenes include simple trichothecenes (i.e., those that have only a central sesquiterpenoid structure) and macrocyclic trichothecenes (i.e., those that have an additional macrocyclic ring), e.g., a verrucarins or roridins, including Verrucarin A, Verrucarin B, Verrucarin J (Satratoxin C), Roridin A, Roridin C, Roridin D, Roridin E (Satratoxin D), Roridin H.

Agents acting as an inhibitor that blocks cellular protein synthesis and/or secretion or organization of extracellular matrix (i.e., an "anti-matrix agent"). Representative examples of "anti-matrix agents" include inhibitors (i.e., agonists and antagonists and competitive and non-competitive inhibitors) of matrix synthesis, secretion and assembly, organizational cross-linking (e.g., transglutaminases cross-linking collagen), and matrix remodeling (e.g., following wound healing). A representative example of a useful therapeutic agent in this category of anti-matrix agents is colchicine, an inhibitor of secretion of extracellular matrix. Another example is tamoxifen for which evidence exists regarding its capability to organize and/or stabilize as well as diminish smooth muscle cell proliferation following angioplasty. The organization or stabilization may stem from the blockage of vascular smooth muscle cell maturation in to a pathologically proliferating form.

Agents that are cytotoxic to cells, particularly cancer cells. Preferred agents are Roridin A, *Pseudomonas* exotoxin and the like or analogs or functional equivalents thereof. A plethora of such therapeutic agents, including radioisotopes and the like, have been identified and are known in the art. In addition, protocols for the identification of cytotoxic moieties are known and employed routinely in the art.

A number of the above therapeutic agents and several others have also been identified as candidates for vascular treatment regimens, for example, as agents targeting restenosis. Such agents are appropriate for the practice of the present invention and include one or more of the following:

Calcium-channel blockers including:
- Benzothiazapines such as diltiazem and clentiazem
- Dihydropyridines such as nifedipine, amlodipine and nicardapine
- Phenylalkylamines such as verapamil Serotonin pathway modulators including:
- 5-HT antagonists such as ketanserin and naftidrofuryl
- 5-HT uptake inhibitors such as fluoxetine Cyclic nucleotide pathway agents including:
- Phosphodiesterase inhibitors such as cilostazole and dipyridamole
- Adenylate/Guanylate cyclase stimulants such as forskolin
- Adenosine analogs Catecholamine modulators including:
- α-antagonists such as prazosin and bunazosine
- β-antagonists such as propranolol
- α/β-antagonists such as labetalol and carvedilol Endothelin receptor antagonists Nitric oxide donors/releasing molecules including:
- Organic nitrates/nitrites such as nitroglycerin, isosorbide dinitrate and amyl nitrite
- Inorganic nitroso compounds such as sodium nitroprusside
- Sydnonimines such as molsidomine and linsidomine
- Nonoates such as diazenium diolates and NO adducts of alkanediamines
- S-nitroso compounds including low molecular weight compounds (e.g., S-nitroso derivatives of captopril, glutathione and N-acetyl penicillamine), high molecular weight compounds (e.g., S-nitroso derivatives of proteins, peptides, oligosaccharides, polysaccharides, synthetic polymers/oligomers and natural polymers/oligomers)
- C-nitroso-, O-nitroso- and N-nitroso-compounds
- L-arginine ACE inhibitors such as cilazapril, fosinopril and enalapril ATII-receptor antagonists such as saralasin and losartan Platelet adhesion inhibitors such as albumin and polyethylene oxide Platelet aggregation inhibitors including:
- Aspirin and thienopyridine (ticlopidine, clopidogrel)
- GP IIb/IIIa inhibitors such as abciximab, epitifibatide and tirofiban Coagulation pathway modulators including:
- Heparinoids such as heparin, low molecular weight heparin, dextran sulfate and β-cyclodextrin tetradecasulfate
- Thrombin inhibitors such as hirudin, hirulog, PPACK (D-phe-L-propyl-L-arg-chloromethylketone) and argatroban
- FXa inhibitors such as antistatin and TAP (tick anticoagulant peptide)
- Vitamin K inhibitors such as warfarin
- Activated protein C Cyclooxygenase pathway inhibitors such as aspirin, ibuprofen, flurbiprofen, indomethacin and sulfinpyrazone Natural and synthetic corticosteroids such as dexamethasone, prednisolone, methprednisolone and hydrocortisone Lipoxygenase pathway inhibitors such as nordihydroguaiaretic acid and caffeic acid Leukotriene receptor antagonists Antagonists of E- and P-selectins Inhibitors of VCAM-1 and ICAM-1 interactions Prostaglandins and analogs thereof including:
- Prostaglandins such as PGE1 and PGI2
- Prostacyclin analogs such as ciprostene, epoprostenol, carbacyclin, iloprost and beraprost Macrophage activation preventers including bisphosphonates HMG-CoA reductase inhibitors such as lovastatin, pravastatin, fluvastatin, simvastatin and cerivastatin Fish oils and omega-3-fatty acids Free-radical scavengers/antioxidants such as probucol, vitamins C and E, ebselen, trans-retinoic acid and SOD mimics Agents affecting various growth factors including:
- FGF pathway agents such as bFGF antibodies and chimeric fusion proteins
- PDGF receptor antagonists such as trapidil
- IGF pathway agents including somatostatin analogs such as angiopeptin and ocreotide
- TGF-β pathway agents such as polyanionic agents (heparin, fucoidin), decorin, and TGF-β antibodies
- EGF pathway agents such as EGF antibodies, receptor antagonists and chimeric fusion proteins
- TNF-α pathway agents such as thalidomide and analogs thereof
- Thromboxane A2 (TXA2) pathway modulators such as sulotroban, vapiprost, dazoxiben and ridogrel
- Protein tyrosine kinase inhibitors such as tyrphostin, genistein and quinoxaline derivatives
- MMP pathway inhibitors such as marimastat, ilomastat and metastat
- Cell motility inhibitors such as cytochalasin B Antiproliferative/antineoplastic agents including:
- Antimetabolites such as purine analogs (6-mercaptopurine), pyrimidine analogs (e.g., cytarabine and 5-fluorouracil) and methotrexate
- Nitrogen mustards, alkyl sulfonates, ethylenimines, antibiotics (e.g., daunorubicin, doxorubicin), nitrosoureas and cisplatin
- Agents affecting microtubule dynamics (e.g., vinblastine, vincristine, colchicine, paclitaxel and epothilone)
- Caspase activators
- Proteasome inhibitors
- Angiogenesis inhibitors (e.g., endostatin, angiostatin and squalamine)
- Rapamycin, cerivastatin, flavopiridol and suramin Matrix deposition/organization pathway inhibitors such as halofuginone or other quinazolinone derivatives and tranilast Endothelialization facilitators such as VEGF and RGD peptide Blood rheology modulators such as pentoxifylline.

In some embodiments, particle 100 can include a combination of any of the above therapeutic agents.

Therapeutic agents are described, for example, in co-pending Published Patent Application No. US 2004/0076582 A1, published on Apr. 22, 2004, and entitled "Agent Delivery Particle", which is incorporated herein by reference, and in Pinchuk et al., U.S. Pat. No. 6,545,097, which is incorporated herein by reference.

Particles 150 can be formed using any of various systems and techniques, such as emulsion polymerization and/or droplet polymerization techniques. Examples of such systems and techniques are described, for example, in co-pending Published Patent Application No. US 2003/0185896 A1, published Oct. 2, 2003, and entitled "Embolization," and in co-pending Published Patent Application No. US 2004/

0096662 A1, published May 20, 2004, and entitled "Embolization," each of which is incorporated herein by reference.

While certain embodiments have been described, other embodiments are also possible.

As an example, particles 150 can include (e.g., encapsulate) diagnostic agent(s) such as a radiopaque material, an MRI-visible material, a ferromagnetic material, and/or an ultrasound contrast agent. For example, particle 150 can encapsulate a ferromagnetic material so that the position of the particle in a lumen can be manipulated with a magnetic field. The magnetic field can be created outside the subject or inside the subject (e.g., via a magnetic catheter). Particles containing diagnostic agents are described in U.S. patent application Ser. No. 10/651,475, filed on Aug. 29, 2003, and entitled "Embolization", and magnetic devices are described in U.S. patent application Ser. No. 10/108,874, filed on Mar. 29, 2002, and entitled "Magnetically Enhanced Injection Catheter," both of which are incorporated herein by reference.

As an additional example, while embodiments have been described in which protective layer 145 is formed of particles, in some embodiments, protective layer 145 is formed of one or more liquid polymers. Examples of polymers from which a liquid polymer can be formed include those noted above. In some embodiments, a liquid polymer can be a carrier fluid for particles. A liquid polymer can be disposed between two portions of tissue using the methods described above (e.g., via a needle, a syringe, or a catheter).

As another example, in some embodiments, protective layer 145 is formed of one or more gels. A gel can be formed of, for example, one or more polymers. Examples of polymers include those noted above. A gel can be disposed between two portions of tissue using the methods described above (e.g., via a needle, a syringe, or a catheter).

As a further example, in some embodiments, protective layer 145 is formed from one or more gases. Examples of gases include helium, neon, argon, krypton, xenon, air, nitrogen, and carbon dioxide. In some embodiments, a gas can be a carrier fluid for particles. A gas can be disposed between two portions of tissue using the methods described above (e.g., via a needle, a syringe, or a catheter).

As an additional example, in some embodiments, protective layer 145 is formed from one or more foams. A foam can be formed of, for example, one or more polymers. Examples of polymers include those noted above. A foam can be disposed between two portions of tissue using the methods described above (e.g., via a needle, a syringe, or a catheter).

As another example, protective layer 145 can be formed of deionized water and/or a buffered saline solution. The buffered saline solution, for example, can include a composition of saline solution and any of various buffers, such as phosphate. In certain embodiments, the deionized water can similarly include a buffer material, such as phosphate. In some embodiments, the deionized water and/or the buffered saline solution can provide an electrical resistance of about 175 kohms or greater (e.g., about 200 kohms or greater, about 225 kohms or greater, about 250 kohms or greater, about 275 kohms or greater, about 300 kohms or greater, about 325 kohms or greater, about 350 kohms or greater). As used herein, the electrical resistance is tested using ASTM D257-99.

As a further example, in certain embodiments, protective layer 145 can be formed of a combination of one or more of the following: deionized water; a buffered saline solution; particles; liquid polymers; gels; gases and/or foams.

As another example, while certain forms of energy have been described, other forms of energy can be used to treat medical conditions. Examples of forms of energy that can be used include microwave energy, ultrasonic energy, laser energy, and/or heat. Similarly, the unhealthy tissue can be cooled. The energy can be administered to the unhealthy tissue using any of various techniques. For example, a probe can be inserted into the unhealthy tissue and activated to release one or more types of energy.

In some embodiments particles including a relatively conductive material (e.g., a ferromagnetic material) can be disposed within the tissue of the subject to enhance the effects of the energy (e.g., RF energy) transmitted to unhealthy tissue 140. In certain embodiments in which particles including a ferromagnetic material have been disposed within the tissue, a magnetic field can be applied to the particles to affect the extent of conductivity. The magnetic field can be varied to adjust the conductivity of the particles (and, therefore, to adjust the extent of heating and ablation caused by the transmitted energy). In some embodiments, the particles can be used in an agitation ablation process. In such a process, a magnetic field can be used to agitate the particles, such that the particles heat and/or physically deform the surrounding tissue, thereby ablating the surrounding tissue. These and other tissue treatment techniques are described in U.S. Pub. Pat. App. No. US-2004-0101564-A1, which is incorporated herein by reference.

As an additional example, while embodiments have been described in which unhealthy liver tissue is treated, other types of unhealthy tissue can also be treated. Examples of other types of tissue that can be treated include bodily vessel tissue, bone tissue, brain tissue, breast tissue, kidney tissue, liver tissue, lung tissue, ovary tissue, prostate tissue, skin tissue, and thyroid tissue.

As a further example, in some embodiments, energy can be used to treat healthy tissue. In some embodiments, for example, the healthy tissue is undesired tissue. For example, energy can be used to treat (e.g., remove) various types of malformed tissue, such as tissue resulting in webbed fingers and/or toes. As a further example, energy can be used to treat various types of malfunctioning tissue. In embodiments in which healthy tissue is treated with energy, it may be desired, for example, to preserve adjacent regions of healthy tissue. Thus, protective layer 145 can be disposed between two regions of healthy tissue.

The medical treatments described herein can similarly be used to treat various other types of medical conditions. For example, in some embodiments, regions of brain tissue may be treated (e.g., destroyed) with electrical stimulation to treat epilepsy. Similarly, regions of nerve tissue may be treated (e.g., destroyed) to treat chronic pain. In certain embodiments, regions of bodily vessel tissue can be treated to occlude the vessel. This can be beneficial, for example, in treating fibroids (e.g., uterine fibroids), varicose veins, alterior venous malformations, and certain forms of trauma.

Other embodiments are in the claims.

What is claimed is:
1. A method, comprising:
disposing a material between a first portion of tissue of a subject and a second portion of tissue of the subject;
separating the first portion of tissue from the second portion of tissue; and
exposing the first portion of tissue to an energy at an intensity sufficient to treat the first portion of tissue, while the material allows the energy to penetrate the second portion of tissue at a reduced energy intensity insufficient to treat the second portion of tissue, wherein the material is selected from at least one member of the group consisting of deionized water, a buffered saline solution, a liquid polymer, a gel, particles, a foam, and a gas; and wherein the first portion of tissue comprises an unhealthy or unwanted tissue and the second portion of tissue comprises a healthy or wanted tissue.

2. The method of claim 1, wherein the second portion of tissue is substantially unexposed to the energy while the first portion of tissue is exposed to the energy.

3. The method of claim 1, wherein the energy comprises at least one member selected from the group consisting of RF energy, microwave energy, ultrasonic energy, laser energy, and heat.

4. The method of claim 1, wherein the first portion of tissue is exposed to the energy by a probe delivered via a catheter.

5. The method of claim 1, wherein:

the first portion of tissue comprises at least one member of the group consisting of bodily vessel tissue, bladder tissue, bone tissue, brain tissue, breast tissue, bronchi tissue, diaphragm tissue, esophagus tissue, gall bladder tissue, heart tissue, intestine tissue, kidney tissue, larynx tissue, liver tissue, lung tissue, lymph vessel tissue, lymph node tissue, nerve tissue, ovary tissue, pancreas tissue, prostate tissue, skin tissue, stomach tissue, thyroid tissue, trachea tissue, urethra tissue, ureter tissue, uterus tissue, and vertebral disc tissue; and the second portion of tissue comprises at least one member of the group consisting of bodily vessel tissue, bladder tissue, bone tissue, brain tissue, breast tissue, bronchi tissue, diaphragm tissue, esophagus tissue, gall bladder tissue, heart tissue, intestine tissue, kidney tissue, larynx tissue, liver tissue, lung tissue, lymph vessel tissue, lymph node tissue, nerve tissue, ovary tissue, pancreas tissue, prostate tissue, skin tissue, stomach tissue, and thyroid tissue, trachea tissue, urethra tissue, ureter tissue, uterus tissue, and vertebral disc tissue.

6. A method, comprising:

disposing a material between a first portion of tissue of a subject and a second portion of tissue of the subject;

separating the first portion of tissue from the second portion of tissue; and exposing the first portion of tissue to an energy at an intensity sufficient to treat the first portion of tissue, while the material allows the energy to penetrate the second portion of tissue at a reduced energy intensity insufficient to treat the second portion of tissue, wherein the material is selected from at least one member of the group consisting of deionized water, a buffered saline solution, a liquid polymer, a gel, particles, a foam, and a gas;

wherein the material comprises particles having at least one of the following characteristics:
a size of at most about 10,000 microns;
a dielectric constant of at least about 2.1; or
a dielectric strength of at least about 100 Kv/mm.

7. The method of claim 1, wherein the material comprises a liquid polymer that comprises at least one member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

8. The method of claim 1, wherein the material comprises a gel that comprises at least one member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

9. The method of claim 1, wherein the material comprises particles that comprise at least one material selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

10. The method of claim 1, wherein the material comprises a foam that comprises at least one member selected from the group consisting of polyvinyl alcohols, polyacrylic acids, polymethacrylic acids, poly vinyl sulfonates, carboxymethyl celluloses, hydroxyethyl celluloses, substituted celluloses, polyacrylamides, polyethylene glycols, polyamides, polyureas, polyurethanes, polyesters, polyethers, polystyrenes, polysaccharides, polylactic acids, polyethylenes, polymethylmethacrylates, polycaprolactones, polyglycolic acids, poly(lactic-co-glycolic) acids, polypropylene, polytetrafluorethylene, polyethyleneterephthalate, polycarbonate, polyphenyleneoxide, polysulfone, polyhydantoine, polyamide-imide, polyimide, cellulose triacetate, and cellulose acetate butyrate.

11. The method of claim 1, wherein the material comprises at least one member selected from the group consisting of water soluble polysaccharides and ionically cross-linkable polymers.

12. The method of claim 1, wherein the material comprises a ceramic material.

13. The method of claim 1, wherein the material is capable of undergoing an endothermic reaction.

14. The method of claim 1, wherein the first portion of tissue comprises one or more of the following: a healthy tissue, an unhealthy tissue, an unwanted tissue, a wanted tissue, a malfunctioning tissue, and a malformed tissue.

15. The method of claim 1, wherein disposing the material between the first and second portions of tissue separates the first portion of tissue from the second portion of tissue.

16. The method of claim 1, wherein separating a first portion of tissue of a subject from a second portion of tissue of the subject creates a space between the first and second portions of tissue.

17. A method, comprising:

disposing a material between a first portion of tissue of a subject and a second portion of tissue of the subject;

separating the first portion of tissue from the second portion of tissue; and exposing the first portion of tissue to an energy at an intensity sufficient to treat the first portion of tissue, while the material allows the energy to penetrate the second portion of tissue at a reduced energy intensity insufficient to treat the second portion of tissue, wherein the material is selected from at least one member of the group consisting of deionized water, a buffered saline solution, a liquid polymer, a gel, particles, a foam, and a gas;

wherein exposing the first portion of tissue to energy comprises cooling the first portion of tissue.

18. The method of claim 6, wherein the first portion of tissue is the same type of tissue as the second portion of tissue.

19. The method of claim 6, wherein disposing the material between the first and second portions of tissue separates the first portion of tissue from the second portion of tissue.

20. A method, comprising:

disposing a material between a first portion of tissue of a subject and a second portion of tissue of the subject; and exposing the first portion of tissue to energy to degrade the first portion of tissue, wherein the second portion of tissue is substantially unharmed while the first portion of tissue is exposed to the energy, a distance between the first and second portions of tissue is at most about five centimeters, and the material is selected from at least one member of the group consisting of deionized water, a buffered saline solution, a liquid polymer, a gel, particles, a foam, and a gas.

* * * * *